(12) United States Patent
Turner et al.

(10) Patent No.: US 7,315,019 B2
(45) Date of Patent: Jan. 1, 2008

(54) ARRAYS OF OPTICAL CONFINEMENTS AND USES THEREOF

(75) Inventors: Stephen Turner, Menlo Park, CA (US); Jonas Korlach, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 322 days.

(21) Appl. No.: 11/228,759

(22) Filed: Sep. 16, 2005

(65) Prior Publication Data

US 2006/0061754 A1    Mar. 23, 2006

Related U.S. Application Data

(63) Continuation-in-part of application No. 10/944,106, filed on Sep. 17, 2004.

(60) Provisional application No. 60/651,846, filed on Feb. 9, 2005, provisional application No. 60/649,009, filed on Jan. 31, 2005.

(51) Int. Cl.
*G02B 6/10* (2006.01)
*H05H 3/04* (2006.01)

(52) U.S. Cl. ............ 250/251; 250/227.14; 250/227.11; 385/129; 385/141; 385/142; 385/144

(58) Field of Classification Search ...................... None
See application file for complete search history.

(56) References Cited

U.S. PATENT DOCUMENTS 4,994,373 A    2/1991    Stavrianopoulos et al.

| | | |
|---|---|---|
| 5,001,050 A | 3/1991 | Blanco et al. |
| 5,198,543 A | 3/1993 | Blanco et al. |
| 5,200,313 A | 4/1993 | Carrico |
| 5,243,618 A | 9/1993 | Dolezal et al. |
| 5,302,509 A | 4/1994 | Cheeseman |
| 5,403,708 A | 4/1995 | Brennan et al. |
| 5,405,747 A | 4/1995 | Jett et al. |
| 5,465,151 A | 11/1995 | Wybourne et al. |
| 5,470,710 A | 11/1995 | Weiss et al. |
| 5,547,835 A | 8/1996 | Koster |
| 5,601,982 A | 2/1997 | Sargent et al. |
| 5,620,854 A | 4/1997 | Holzrichter et al. |
| 5,631,134 A | 5/1997 | Cantor |

(Continued)

FOREIGN PATENT DOCUMENTS

EP    0745686 A1    12/1996

(Continued)

OTHER PUBLICATIONS

Chatterjee, et al., "Cloning and overexpression of the gene encoding bacteriophage T5 DNA polymerase," *Gene*. 1991; 97:13-19.

(Continued)

*Primary Examiner*—Nikita Wells
(74) *Attorney, Agent, or Firm*—Wilson Sonsini Goodrich & Rosati

(57) ABSTRACT

The present invention relates to optical confinements, methods of preparing and methods of using them for analyzing molecules and/or monitoring chemical reactions. The apparatus and methods embodied in the present invention are particularly useful for high-throughput and low-cost single-molecular analysis.

47 Claims, 16 Drawing Sheets

U.S. PATENT DOCUMENTS

| | | |
|---|---|---|
| 5,646,264 A | 7/1997 | Glazer et al. |
| 5,661,028 A | 8/1997 | Foote |
| 5,677,196 A | 10/1997 | Herron et al. |
| 5,677,769 A | 10/1997 | Bendett |
| 5,688,648 A | 11/1997 | Mathies et al. |
| 5,695,934 A | 12/1997 | Brenner |
| 5,703,222 A | 12/1997 | Grossman et al. |
| 5,846,727 A | 12/1998 | Soper et al. |
| 5,854,033 A | 12/1998 | Lizardi |
| 5,858,671 A | 1/1999 | Jones |
| 5,922,591 A | 7/1999 | Anderson et al. |
| 5,961,923 A | 10/1999 | Nova et al. |
| 6,004,744 A | 12/1999 | Goelet et al. |
| 6,027,890 A | 2/2000 | Ness et al. |
| 6,048,690 A | 4/2000 | Heller et al. |
| 6,210,896 B1 | 4/2001 | Chan |
| 6,221,592 B1 | 4/2001 | Schwartz et al. |
| 6,232,075 B1 | 5/2001 | Williams et al. |
| 6,255,083 B1 | 7/2001 | Williams et al. |
| 6,263,286 B1 | 7/2001 | Gilmanshin et al. |
| 6,280,939 B1 | 8/2001 | Allen |
| 6,287,824 B1 | 9/2001 | Lizardi |
| 6,306,607 B2 | 10/2001 | Williams et al. |
| 6,323,009 B1 | 11/2001 | Lasken et al. |
| 6,325,553 B1 | 12/2001 | Deacon et al. |
| 6,355,420 B1 | 3/2002 | Chan |
| 6,399,335 B1 | 6/2002 | Kao et al. |
| 6,403,311 B1 | 6/2002 | Chan |
| 6,485,944 B1 | 11/2002 | Church et al. |
| 6,510,263 B1 | 1/2003 | Maisenholder et al. |
| 6,515,751 B1 | 2/2003 | Craighead et al. |
| 6,524,829 B1 | 2/2003 | Seeger |
| 6,528,780 B1 | 3/2003 | Mitsuoka et al. |
| 6,573,089 B1 | 6/2003 | Vann |
| 6,617,137 B2 | 9/2003 | Dean et al. |
| 6,618,537 B2 | 9/2003 | Temkin et al. |
| 6,642,034 B2 | 11/2003 | Lizardi |
| 6,670,126 B2 | 12/2003 | Kingsmore et al. |
| 6,713,672 B1 | 3/2004 | Stickney |
| 6,740,865 B1 | 5/2004 | Rushbrook et al. |
| 6,753,200 B2 | 6/2004 | Craighead et al. |
| 6,961,125 B2 | 11/2005 | Rushbrooke et al. |
| 7,170,050 B2 | 1/2007 | Turner et al. |
| 2001/0014850 A1 | 8/2001 | Gilmanshin et al. |
| 2001/0029049 A1 | 10/2001 | Walt et al. |
| 2002/0025529 A1 | 2/2002 | Quake et al. |
| 2002/0110939 A1 | 8/2002 | Miki et al. |
| 2002/0164629 A1 | 11/2002 | Quake et al. |
| 2002/0180570 A1 | 12/2002 | Facer et al. |
| 2003/0044781 A1 | 3/2003 | Korlach et al. |
| 2003/0064366 A1 | 4/2003 | Hardin et al. |
| 2003/0092034 A1 | 5/2003 | Cooper et al. |
| 2003/0123827 A1 | 7/2003 | Salerno et al. |
| 2003/0137313 A1 | 7/2003 | Jannsen et al. |
| 2003/0148542 A1 | 8/2003 | Pawlak et al. |
| 2003/0174992 A1* | 9/2003 | Levene et al. ............... 385/129 |
| 2003/0175780 A1 | 9/2003 | Jones |
| 2003/0186255 A1 | 10/2003 | Williams et al. |
| 2003/0194740 A1 | 10/2003 | WIlliams et al. |
| 2004/0110180 A1 | 6/2004 | Recipon et al. |
| 2004/0132155 A1 | 7/2004 | Plowman et al. |
| 2004/0157306 A1 | 8/2004 | Plowman et al. |
| 2004/0203097 A1 | 10/2004 | Yue et al. |
| 2005/0196317 A1 | 9/2005 | Walt et al. |
| 2006/0017917 A1 | 1/2006 | Cullum et al. |
| 2006/0061755 A1 | 3/2006 | Turner et al. |
| 2006/0062531 A1 | 3/2006 | Turner et al. |
| 2006/0063264 A1 | 3/2006 | Turner et al. |
| 2007/0206189 A1 | 9/2007 | Turner et al. |

FOREIGN PATENT DOCUMENTS

| | | |
|---|---|---|
| EP | 0258 017 B1 | 6/1997 |
| EP | 0834 576 A2 | 4/1998 |
| WO | WO 90/13666 | 11/1990 |
| WO | WO 91/13075 | 9/1991 |
| WO | WO 93/21340 A1 | 10/1993 |
| WO | WO 95/06138 | 3/1995 |
| WO | WO 96/27025 | 9/1996 |
| WO | WO 98/44152 | 10/1998 |
| WO | WO 99/05315 | 2/1999 |
| WO | WO 99/19341 | 4/1999 |
| WO | WO 00/06770 | 2/2000 |
| WO | WO 00/09757 | 2/2000 |
| WO | WO 00/36151 | 6/2000 |
| WO | WO 00/36152 | 6/2000 |
| WO | WO 00/40750 | 7/2000 |
| WO | WO 00/53805 | 9/2000 |
| WO | WO 00/53812 | 9/2000 |
| WO | WO 00/58507 | 10/2000 |
| WO | WO 00/60072 | 10/2000 |
| WO | WO 00/60114 | 10/2000 |
| WO | WO 01/13088 A1 | 2/2001 |
| WO | WO 01/16375 A2 | 3/2001 |
| WO | WO 01/23610 | 4/2001 |
| WO | WO 01/25480 | 4/2001 |
| WO | WO 01/32930 | 5/2001 |
| WO | WO 01/57248 | 8/2001 |
| WO | WO 01/57249 | 8/2001 |
| WO | WO 01/94609 | 12/2001 |
| WO | WO 02/02813 | 1/2002 |
| WO | WO 02/03305 | 1/2002 |
| WO | WO 02/29106 | 4/2002 |
| WO | WO 02/061126 | 8/2002 |
| WO | WO 02/061127 | 8/2002 |
| WO | WO 02/072892 | 9/2002 |
| WO | WO 02/095070 | 11/2002 |
| WO | WO 02/101095 | 12/2002 |
| WO | WO 03/010289 | 2/2003 |
| WO | WO 03/016565 | 2/2003 |
| WO | WO 03/020734 | 3/2003 |
| WO | WO 03/089931 A1 | 10/2003 |

OTHER PUBLICATIONS

Craighead, H.G. "Nanoelectromechanical Systems," *Science*. 2000; 290: 1532-1535.

Davis et al., "Rapid DNA Sequencing Based Upon Single Molecule Detection," *Genetic Analysis Techniques and Applications*. 1991; 8(1):1-7.

Dobrikov, et al., "Sensitized Photomodification of Single-Stranded DNA by a Binary System of Oligonucleotide Conjugates," *Antisense & Nucleic Acid Drug Development*. 1997; 7:309-317.

Dörre, et al., "Techniques for Single Molecule Sequencing," *Bioimaging*. 1997; 5:139-152.

Dörre, K., et al., "Highly Efficient Single Molecule Detection in Microstructures," *Journal of Biotechnology*. 2001; 86(3):225-236.

Foquet, et al., "Fabrication of Microcapillaries and Waveguides for Single Molecule Detection," *SPIE*. 1998; 3258:(0277-786X) 141-147.

Harding, et al., "Single-Molecule Detection as an Approach to Paid DNA Sequencing," *Trends in Biotechnol*. 1992; 10:55-57.

Heinze, K.G., et al., "Two-photon Flourescence Coincidence Analysis: Rapid measurements of enzyme kinetics," *Biophysical Journal*. 2002; 83(3):1671-1681.

Jackson, John D., "Classical Elecytrodynamics," Second Edition, John Willey and Sons; 1975.

Jacobsen, et al., "The N-Terminal Amino-Acid Sequences of DNA Polymerase I from *Escherichia coli* and of the Large and the Small Fragments Obtained by a Limited Proteolysis," *Eur. J. Biochem*. 1974; 45:623-627.

Jung, et al., "Bacteriophage PRDI DNA polymerase: Evolution of DNA polymerases," *Proc. Natl. Aced. Sci. USA.* 1987; 84:8287-8291.

Kaboord, et al., "Accessory proteins function as matchmakers in the assembly of the T4 DNA polymerase holoenzyme," *Current Biology.* 1995; 5:149-157.

Kang, et al., "Investigations of Potential—Dependent Fluxes of Ionic Permeates in Gold Nanotubule Membranes Prepared Via the Template Method," *Langmuir.* 2001; 17 (9):2753-2759.

Kawata, et al., "Feasibility of Molecular-Resolution Fluorescence Near-Field Microscopy Using Multi-Photon Absorption and Field Enhancement Near a Sharp Tip," *Journal of Applied Physics.* 1999; 85(3):1294-1301.

Kristensen, et al., "Rapid and Simple Preparation of Plasmids Suitable for Dideoxy DNA Sequencing and Other Purposes," *DNA Sequence.* 1991; 1:227-232.

Levene, et al., "Zero-Mode Waveguides for Single-Molecule Analysis at High Concentrations," *Science.* 2003; 299:682-686.

Lopez, et al., "Subwavelength Surface-Relief Gratings Fabricated by Microcontact Printing of Self-Assembled Monolayers," *Applied Optics.* 2001; 40 (13):2068-2075.

Matsumoto, et al., "Primary structure of bacteriophage M2 DNA polymerase: conserved segments within protein-priming DNA polymerases and DNA polymerase I of *Escherichia coli*," *Gene.* 1989; 84:247-255.

McDonald, et al., "Fabrication of a Configurable, Single-Use Microfluidic Device," *Analytical Chemistry.* 2001. 73 (23):5645-5650.

Mendez, et al., "Protein-primed DNA replication: a transition between two modes of priming by a unique DNA polymerase," *The EMBO Journal.* 1997; 16 (9):2519-2527.

Nickerson, et al., "PolyPhred: Automating the Detection and Genotyping of Single Nucleotide Substitutions Using Fluorescence-Based Resequencing," *Nucleic. Acids Research.* 1997; 25 (14):2745-2751.

Novotny, et al., "Theory of Nanometric Optical Tweezers," *Physical Review Letters.* 1997; 79 (4):645-648.

Rigler, et al., "Differences in the Mechanism of Stimulation of T7 DNA Polymerase by Tow Binding Modes of *Escherichia coli* Single-stranded DNA-binding Protein," *Journal of Biological Chemistry.* 1995; 270 (15):8910-8919.

Sanchez, et al., "Near-Field Fluorescence Microscopy Based on Two-Photon Excitation with Metal Tips," *Physical Review Letters.* 1999; 82 (20):4014-4017.

Schwille, P., et al., "Dual-Color Fluorescence Cross-Correlation Spectroscopy For Multicomponent Diffusional Analysis in Solution," *Biophysical Journal.* 1997; 72:1878-1886.

Siegal, et al., "A Novel DNA Helicase from Calf Thymus," *Journal of Biological Chemistry.* 1992; 267 (19):13629-13635.

Skaliter, et al., "Rolling circle DNA replication in vitro by a complex of herpes simplex virus type 1-encoded enzymes," *Proc. Natl, Acad. Sci. USA.* 1994; 91:10665-10669.

Voss, et al., "Automated Cycle Sequencing with Taquenase™ : Protocols for Internal Labeling, Dye Primer and "Doublex" Simultaneous Sequencing," *BioTechniques.* 1997; 23 (2):312-318.

Webb, et al., "Nonlinear magic: multiphoton microscopy in the biosciences," *Nature Biotecnology.* 2003; 21 (11):1369-1377.

Weiss, S., "Fluorescence Spectroscopy of Single Biomolecules," *Science.* 1999; 283:1676-1683.

Zhu, et al., "Purification and characterization of PRD1 DNA polymerase," *Biochimica et Biophysica Acta.* 1994; 1219:267-276.

Zijderveld, et al., "Helix-Destabilizing Properties of the Adenovirus DNA-Binding Protein," Journal of Virology. 1994; 68 (2):1158-1164.

Eggeling, et al. Monitoring Conformational Dynamics Of A Single Molecule By Selective Fluorescence Spectroscopy. *Proc. Natl. Acad. Sci. USA.* 1998; 95:1556-1561.

Goodwin, et al. Application of Single Molecule Detection to DNA Sequencing. *Nucleosides & Nucleotides.* 1997; 16(5&6): 543-550.

Ronaghi, et al. A Sequencing Method Based on Real-Time Pyrophosphate. *Science.* 1998; 281: 363, 365.

Sanger, et al. DNA sequencing with chain-terminating inhibitors. *Proc. Natl. Acad. Sci. USA.* 1997; 74(12): 5463-5467.

\* cited by examiner

A

B

A)

B)

C)

a.) Example of a photocleavable blocker:
1-(aminomethyl-2-nitrophenyl) ethyl carbonate cleavage occurs around 340 nm b.)

cleavage wavelength 350 nm c.)

d.)

ARRAYS OF OPTICAL CONFINEMENTS AND USES THEREOF

CROSS REFERENCE TO RELATED APPLICATION

This application is a continuation-in-part of U.S. Utility patent application Ser. No. 10/944,106, filed Sep. 17, 2004, pending, which is hereby incorporated herein by reference in its entirety for all purposes. This application also claims priority to U.S. Provisional Application Nos. 60/649,009 and 60/651,846 filed on Jan. 31, 2005 and Feb. 9, 2005, respectively, both of which are incorporated herein by reference for all purposes.

BACKGROUND OF THE INVENTION

Confinement of illumination and signal detection has long been recognized as an important tool in molecular diagnostics since the application of Fluorescence Correlation Spectroscopy (FCS). FCS involves illumination of a sample volume containing fluorophore-labeled molecules, and detection of fluctuations in fluorescence signal produced by the molecules as they diffuse into and out of an effective observation volume. The fluorescence intensity fluctuations can best be analyzed if the volume under observation contains only a small number of fluorescent molecules, and if the background signal is low. This can be accomplished by the combination of a drastically limited detection volume and a low sample concentration. The detection volume of traditional FCS is approximately 0.5 femtoliters (or $0.5 \times 10^{-15}$ liters), and is achieved through the use of a high numerical aperture microscope objective lens to tightly focus a laser beam. In this detection volume, single molecules can be observed in solutions at concentrations of up to approximately one nanomolar. This concentration range is unacceptably low for most biochemical reactions, which have reaction constants that are typically in or above the micromolar range. At lower concentrations, these reactions either do not proceed acceptably fast, or behave in a qualitatively different fashion than is useful in most analyses. To observe single molecules at higher, more relevant concentrations, the observation volume would typically need to be reduced to far smaller dimensions.

In recent years, the advancement in nanofabrication technology enabled the production of nanoscale devices that are integrated with electrical, optical, chemical and/or mechanical elements.

However, there still remains a considerable need for chemical and biological analyses that are faster, cheaper and of greater accuracy, to provide for the ability to observe single molecule reactions under conditions that are more biologically or diagnostically relevant. There also exists a need for small, mass produced, and disposable devices that can aid in these goals by providing optical confinements that are amenable to single-molecule analysis at a higher concentration. The present invention satisfies these needs and provides related advantages as well.

SUMMARY OF THE INVENTION

A principal aspect of the present invention is the design of optical devices and methods for characterizing molecules and/or monitoring chemical reactions. The devices and methods of the present invention are particularly suited for single-molecule analysis.

Accordingly, the present invention provides an array of optical confinements having a surface density exceeding $4 \times 10^4$ confinements per $mm^2$, preferably exceeding $10^5$ confinements per $mm^2$. In one aspect, the individual confinement in the array provide an effective observation volume that is less than one nanoliter ($10 \times^{-9}$ liter), less than one picoliter, or less than one femtoliter, preferably on the order of zeptoliter. In other aspects, each of the individual confinement provides an effective observation volume that is less than 1000 zeptoliters, 100 zeptoliters, 80 zeptoliters, or less than 50 zeptoliters, or even less than 10 zeptoliters.

In other aspects, each of the individual confinement yields an effective observation volume that permits resolution of individual molecules present at a concentration that is higher than one nanomolar, or higher than 100 nanomolar, or on the order of micromolar range. In certain preferred aspects, each of the individual confinement yields an effective observation volume that permits resolution of individual molecules present at a physiologically relevant concentration, e.g., at a concentration higher than about 1 micromolar, or higher than 50 micromolar range or even higher than 100 micromolar. The array may comprise a zero-mode waveguide or other nanoscale optical structure. The array of optical confinements may further comprise another array of confinements that does not yield the above-described effective observation volume or does not permit resolution of individual molecules. For example, the array of optical confinements may be coupled with or integrated into a microtiter plate, where a separate array of optical confinements may be disposed within each of several different wells on a multi-well reaction plate. The array of optical confinement may comprise at least about $2 \times 10^5$ optical confinement, or at least about $10^6$, or at least about $10^7$ optical confinements.

In another embodiment, the present invention provides a method of creating a plurality of optical confinements having the aforementioned characteristics. The method involves the steps of (a) providing a substrate; and (b) forming an array of optical confinements having a surface density exceeding $4 \times 10^4$ confinements per $mm^2$, wherein the individual confinement comprises a zero-mode waveguide comprising: a cladding surrounding a core, wherein said cladding is configured to preclude propagation of electromagnetic energy of a wavelength longer than a cutoff wavelength longitudinally through the core of the zero-mode waveguide; and (c) illuminating the array with an electromagnetic radiation of a frequency less than the cutoff frequency, thereby creating the plurality of optical confinements.

In another embodiment, the present invention provides a method of creating an optical observation volume that permits resolution of individual molecules. The method involves providing a zero-mode waveguide that comprises a cladding surrounding a core, wherein said cladding is configured to preclude propagation of electromagnetic energy of a frequency less than a cutoff frequency longitudinally through the core of the zero-mode waveguide, wherein upon illuminating the zero-mode waveguide with an electromagnetic radiation of a frequency less than the cutoff frequency, the zero-mode waveguide yields an effective observation volume that permits resolution of individual molecules. In certain aspects, the effective observation volume is less than one nanoliter ($10^{-9}$ liter), less than one picoliter, or less than one femtoliter, preferably on the order of zeptoliters. Using the zero-mode waveguide of the present invention, one typically can obtain an effective observation volume that is less than 100 zeptoliter ($100 \times 10^{-21}$ liters) or less than 50 zeptoliters, or even less than 10 zeptoliters. In other method yields an effective observation volume that permits resolution of individual molecules present at a concentration that is higher than one nanomolar, more often higher than 100 nanomolar, and preferably on the order of micromolar range. In preferred embodiments, individual molecules present at a concentration higher than about 5 micromolar, or higher than 7.5 micromolar, or even higher than 50 micromolar range, can be resolved by the method of the present invention.

The present invention also provides a method of detecting interactions among a plurality of molecules. The method comprises the steps of (a) placing the plurality of molecules in close proximity to an array of zero-mode waveguides, wherein individual waveguides in the array are separated by a distance sufficient to yield detectable intensities of diffractive scattering at multiple diffracted orders upon illuminating the array with an incident wavelength; (b) illuminating the array of zero-mode waveguides with an incident wavelength; and (c) detecting a change in the intensities of diffractive scattering of the incident wavelength at the multiple diffracted orders, thereby detecting the interactions among a plurality of molecules.

The present invention also provides a method of reducing diffractive scattering upon illuminating an array of optical confinements with an incident wavelength, wherein the array comprises at least a first optical confinement and a second optical confinement, said method comprising: forming the array of optical confinements wherein the optical confinement is separated from the second optical confinement by a distance such that upon illumination with the incident wavelength, intensity of diffractive scattering resulting from the first optical confinement at a given angle is less than that if the first optical confinement were illuminated with the same incident wavelength in the absence of the optical confinement. In preferred aspects, the aforementioned optical confinements are zero mode waveguides.

The present invention also includes a method of detecting a biological analyte using an array of optical confinements having a density on a substrate exceeding $4 \times 10^4$ confinements per $mm^2$ or any other density described herein or equivalents thereof. The method typically involves illuminating at least one optical confinement within the array that is suspected to contain the analyte with an incident light beam. The invention also provides a method of using of an array of optical confinements having a density on a substrate exceeding $4 \times 10^4$ confinements per $mm^2$ any other density described herein or equivalents thereof for performing multiple chemical reactions. The method comprises the steps of placing the plurality of reaction samples comprising labeled reactants into the optical confinements in the array, wherein a separate reaction sample is placed into a different confinement in the array; subjecting the array to conditions suitable for formation of products of the chemical reactions; and detecting the formation of the products with said optical system.

In addition, the invention provides a method of sequencing a plurality of target nucleic acid molecules. The method typically involves (a) providing an array of optical confinements having a density on a substrate exceeding $4 \times 10^4$ confinements per $mm^2$, or any other density described herein or equivalents thereof, wherein said optical confinements provide an effective observation volume that permits observation of individual molecules; and an optical system operatively coupled to the optical confinements that detects signals from the effective observation volume of said confinement; (b) mixing in the optical confinements the plurality of target nucleic acid molecules, primers complementary to the target nucleic acid molecules, polymerization enzymes, and more than one type of nucleotides or nucleotide analogs to be incorporated into a plurality of nascent nucleotide strands, each strand being complementary to a respective target nucleic acid molecule; (c) subjecting the mixture of step (b) to a polymerization reaction under conditions suitable for formation of the nascent nucleotide strands by template-directed polymerization of the nucleotides or nucleotide analogs; (d) illuminating the optical confinements with an incident light beam; and (e) identifying the nucleotides or the nucleotide analogs incorporated into the each nascent nucleotide strand.

The present invention also provides an apparatus comprising an array of waveguides on a solid support having a fill fraction greater than about 0.0001, wherein said waveguides are suitable for holding a biological reagent, and wherein waveguides provide an effective observation volume that permits observation of individual molecules present in said biological reagent; and an optical system that detects said individual molecules in said waveguides, by e.g., detecting signals from the effective observation volume. In one aspect, the array has a fill fraction greater than about 0.001. In another aspect, the array has a fill fraction greater than about 0.01, in some instances greater than 0.1, or within the range about 0.001 to about 0.1.

The present invention also provides various methods of using such high fill fraction array. In one embodiment, the present invention provides a method of detecting a biological analyte. The method comprises optically capturing the analyte within an optical confinement that is created by (a) providing an array of waveguides having a fill fraction greater than about 0.0001; and (b) illuminating at least one waveguide within the array that is suspected to contain the analyte with an incident light beam thereby detecting the analyte.

In another embodiment, the present invention provides a method of performing multiple chemical reactions involving a plurality of reaction samples using the subject high fill fraction array. The method involves (a) providing a subject high fill fraction array; (b) placing the plurality of reaction samples comprising labeled reactants into the waveguides in the array, wherein a separate reaction sample is placed into a different waveguide in the array; (c) subjecting the array to conditions suitable for formation of products of the chemical reactions; and (d) detecting the formation of the products with an optical system. The step of detecting may comprise illuminating the different waveguides with an incident light beam and detecting an optical signal emitted from the reaction samples. Applicable chemical reactions may involve protein-protein interactions, nucleic acid-protein interactions, and nucleic acid-nucleic acid interactions. Specifically, the present invention provides a method of sequencing a plurality of target nucleic acid molecule using a fill fraction greater than about 0.0001.

The present invention further provides a method of sequencing nucleic acid using an array having a high fill faction. The method typically involves a) providing an array of waveguides having a fill fraction greater than about 0.0001, or 0.001, or 0.01 or even 0.1; (b) mixing in the waveguides the plurality of target nucleic acid molecules, primers complementary to the target nucleic acid molecules, polymerization enzymes, and more than one type of nucleotides or nucleotide analogs to be incorporated into a plurality of nascent nucleotide strands, each strand being complementary to a respective target nucleic acid molecule; (c) subjecting the mixture of step (b) to a polymerization reaction under conditions suitable for formation of the nascent nucleotide strands by template-directed polymerization of the nucleotides or nucleotide analogs; (d) illuminating the waveguides with an incident light beam; and (e) identifying the nucleotides or the nucleotide analogs incorporated into the each nascent nucleotide strand.

Also included in the present invention is a redundant sequencing method. The method comprises (a) subjecting a target nucleic acid molecule to a template-directed polymerization reaction to yield a nascent nucleic acid strand that is complementary to the target nucleic acid molecule in the presence of a plurality of types of nucleotides or nucleotide analogs, and a polymerization enzyme exhibiting strand-displacement activity; and (b) registering a time sequence of incorporation of nucleotides or nucleotide analogs into the nascent nucleotide strand.

In one aspect of this embodiment, the target nucleic acid molecule is a circular nucleic acid, or is a linear or circular template strand synthesized from a circular nucleic acid sequence such that the synthesized strand includes multiple repeated copies of the original circular strand, and is thus is subject to the sequencing operations of the invention. In another aspect of this embodiment, the target nucleic acid molecule is sequenced multiple times, e.g., more than once, or more than twice by the polymerization enzyme. In yet another aspect of this embodiment, the polymerization enzyme is a DNA polymerase, such as a modified or unmodified Φ29 polymerase.

Further included in the present invention is a solid support having a surface wherein the surface has a polymerization enzyme array attached to it, wherein members of the array comprise individually and optically resolved polymerization enzymes possessing strand-displacement activities.

Also provided is a zero mode waveguide, comprising a first molecular complex immobilized therein, said molecular complex comprising a polymerization enzyme complexed with a target nucleic acid, wherein the polymerization enzyme processes a sequence of nucleotides in said target nucleic acid multiple times via template-dependent replication of the target nucleic acid.

Further provided by the present invention is a method of fabricating an array of optical confinements that exhibits a minimal intensity of diffractive scattering of an incident wavelength. The method comprises providing a substrate; and forming the array of optical confinements on the substrate such that individual confinements in the array are separated from each other at a distance less than one half of the wavelength.

Finally, the present invention includes a method of fabricating an optical confinement the method comprises a cladding surrounding a core, comprising: (a) providing a substrate coated with a layer of photoresist; (b) patterning said layer of photoresist to define boundaries of said core; (c) removing said layer of photoresist surrounding said defined boundaries so that a sufficient amount of photoresist remains to occupy said core; (d) depositing a layer of cladding material over said remaining photoresist and said substrate; (e) removing at least a portion of said cladding material deposited over said remaining photoresist; and (f) removing said photoresist of step (e) to form said core surrounded by said cladding of said optical confinement. In one aspect, the photoresist is negative and said patterning step employs a positive pattern. In another aspect, the photoresist is positive and said patterning step employs a negative pattern. The removing step can be effected by a technique selected from the group consisting of etching, mechanical polishing, ion milling, and solvent dissolution. The layer of cladding material can be deposited by a thermal evaporation method or vapor deposition.

DETAILED DESCRIPTION OF THE INVENTION

Figure 1:
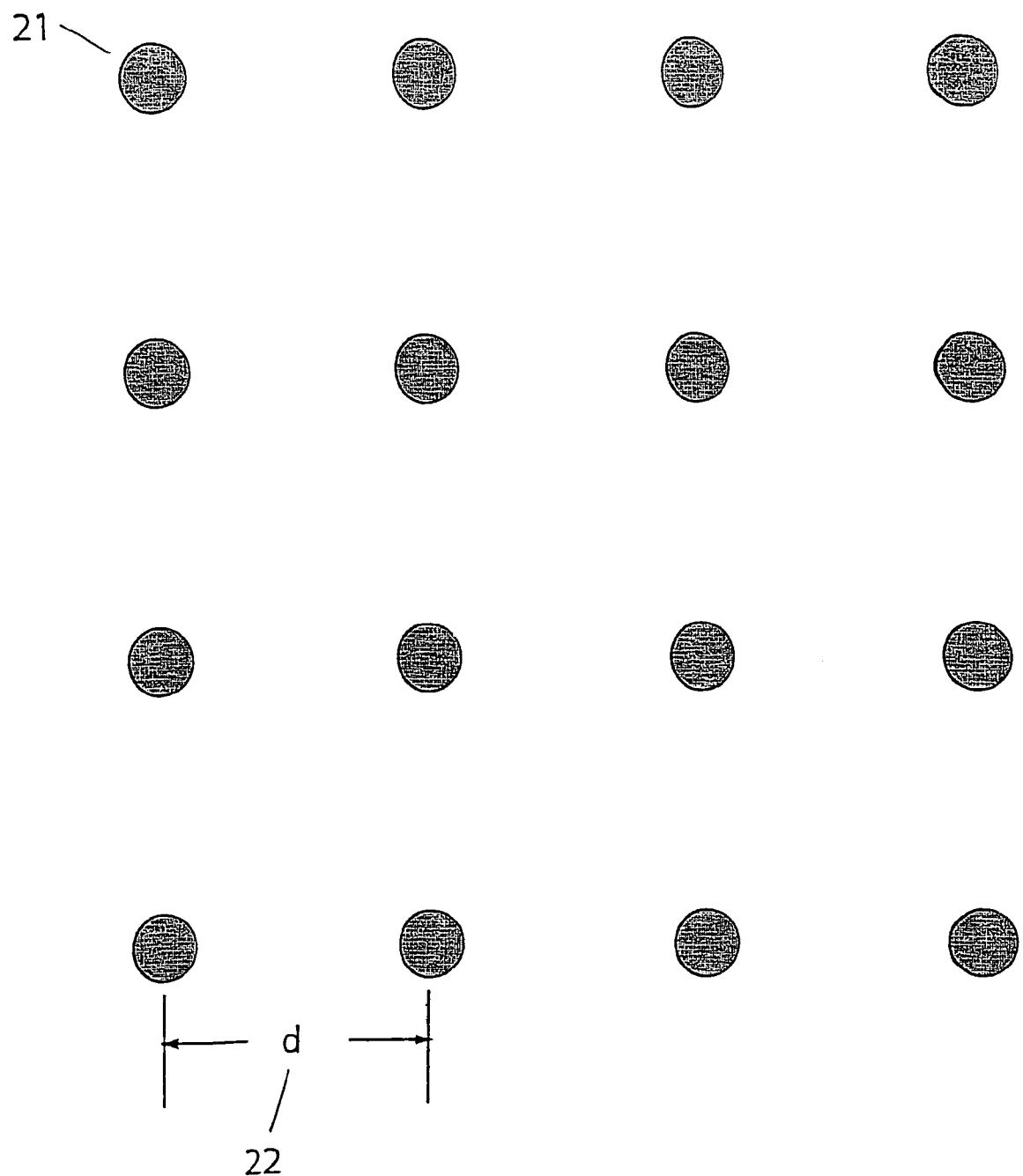
FIG. 1 depicts a top view of an array of illustrative optical confinements, here zero-mode waveguides arranged in a square format.

The practice of the present invention will employ, unless otherwise indicated, conventional techniques of Integrated Circuit (IC) processing biochemistry, chemistry, molecular biology, genomics and recombinant DNA, which are within the skill of the art. See, e.g., Stanley Wolf et al., SILICON PROCESSING FOR THE VLSI ERA, Vols 1-4 (Lattice Press); Michael Quirk et al., SEMICONDUCTOR MANUFACTURING TECHNOLOGY; Sambrook, Fritsch and Maniatis, MOLECULAR CLONING: A LABORATORY MANUAL, $2^{nd}$ edition (1989); the series METHODS IN ENZYMOLOGY (Academic Press, Inc.): PCR 2: A PRAC- TICAL APPROACH (M. J. MacPherson, B. D. Hames and G. R. Taylor eds. (1995), all of which are incorporated herein by reference.

Definitions

As used in the specification and claims, the singular form "a", "an" and "the" include plural references unless the context clearly dictates otherwise.

"Luminescence" refers to the emission of light from a substance for any reason other than a rise in its temperature. In general, atoms or molecules emit photons of electromagnetic energy (e.g., light) when then move from an "excited state" to a lower energy state (usually the ground state); this process is often referred to as "decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin allowed transitions. If photoluminescence is the result of a spin forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" or "luminescent signal" may have any one of the above-described properties.

The term "electromagnetic radiation" refers to electromagnetic waves of energy including, for example, in an ascending order of frequency (or alternatively, in a descending order of wavelength), infrared radiation, visible light, ultraviolet (UV) light, X-rays, and gamma rays.

As used herein, an "effective observation volume" typically refers to that volume that is observable by the detection means employed for a given application. For example, in the case of fluorescence based detection, it is that volume which is exposed to excitation radiation and/or from which emission radiation is gathered by an adjacent optical train/detector. By way of example, in the case of a zero mode waveguide used for certain applications, an effective observation volume is dictated by the propagation of excitation radiation into the waveguide core, and particularly that volume that is exposed to light that is at least 1%, and preferably at least 10% of the original intensity of excitation radiation entering the waveguide core. Such intensities and volumes are readily calculable from the particular conditions of the application in question, including the wavelength of the excitation radiation and the dimensions of the waveguide core (See, e.g., U.S. Pat. No. 6,917,726, incorporated herein by reference in its entirety for all purposes).

A "primer" is a short polynucleotide, generally with a free 3' OH group, that binds to a target nucleic acid (or template) potentially present in a sample of interest by hybridizing with the target nucleic acid, and thereafter promoting polymerization of a polynucleotide complementary to the target.

The terms "operatively linked to" or "operatively coupled to" are used interchangeably herein. They refer to a juxtaposition wherein the components so described are in a relationship permitting them to function in their intended manner.

The term "nucleotide" generally refers to a molecule comprising a base, sugar and one or more anionic groups, preferably phosphates. The molecule may comprise one, two, three, four, five or more phosphates groups and/or other groups such as sulfate. The term also encompasses nucleotide analogs that are structurally analogous to naturally occurring nucleotides and are capable of acting substantially like nucleotides, for example exhibiting base complementarity with one or more of the bases that occur in DNA or RNA, and/or being capable of base-complementary incorporation in synthesizing nucleotide strand by a polymerization enzyme.

The term "polynucleotide" refers to a polymeric form of "nucleotides" of any length.

A "type of nucleotide" refers to a set of nucleotides that share a common characteristic that is to be detected. For instance, the types of nucleotides can be classified into four categories: A, T, C, and G for DNA, or A, U, C and G for RNA. In some embodiments, each type of nucleotides used in the a reaction will be labeled with a unique label that is distinguishable from the rest.

The term "optical confinement" refers to an area in which the reactants for an intended reaction within the confinement are confined and resolved by optical means.

A "polynucleotide probe" refers to a polynucleotide used for detecting or identifying its corresponding target polynucleotide in a hybridization reaction.

The term "hybridize" as applied to a polynucleotide refers to the ability of the polynucleotide to form a complex that is stabilized via hydrogen bonding between the bases of the nucleotide residues in a hybridization reaction. The hydrogen bonding may occur by Watson-Crick base pairing, Hoogstein binding, or in any other sequence specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

Hybridization can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second.

"Complementarity" or "homology" (the degree that one polynucleotide is complementary with another) is quantifiable in terms of the proportion of bases in opposing strands that are expected to form hydrogen bonding with each other, according to generally accepted base pairing rules.

Structure of the Optical Confinements of the Present Invention

One aspect of the present invention is the design of optical devices and methods for characterizing molecules and/or monitoring chemical reactions. The optical devices of the present invention allow multiplexing of large numbers of single-molecule analyses under physiologically relevant conditions.

In one embodiment, the present invention provides a high density array of optical confinements having a surface density exceeding $4 \times 10^4$ confinements per $mm^2$, preferably exceeding $10^5$, wherein the individual confinement in the array provides an effective observation volume on the order of zeptoliters. The array may contain at least about $2 \times 10^5$, at least about $10^6$, or at least about $10^7$ optical confinements. Preferably, the individual confinement in the array provides an effective observation volume less than about 1000 zeptoliters, more preferably less than about 900, more preferably less than about 80, even more preferably less than about 10 zeptoliters. Where desired, an effective observation volume less than 1 zeptoliter can be provided. In a preferred aspect, the individual confinement yields an effective observation volume that permits resolution of individual molecules present at a physiologically relevant concentration. The physiologically relevant concentrations for most biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu M$), or more preferably higher than 50 $\mu M$, or even higher than 100 $\mu M$.

To achieve the required observation volume for single-molecule analysis under physiologically relevant conditions, the array may comprise zero-mode waveguides or alternative nanoscale optical structures. Such alternative structures include but are not limited to porous films with reflective index media, and confinements using index matching solids.

As used herein, "zero-mode waveguide" refers to an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single molecules, even when they are present at a concentration as high as in the micromolar range.

The zero-mode waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation. Suitable materials for fabricating the cladding include but are not limited to alloys, metals, and semi-conducting materials, and any combination thereof. Alloys include any of the numerous substances having metallic properties but comprising two or more elements of which at lest one is a metal. Alloys may vary in the content or the amount of the respective elements-whether metallic or non metallic. Preferred alloys generally improve some desirable characteristics of the material over a pure elemental material. Characteristics that can be improved through the use of mixtures of materials include, chemical resistance, thermal conductivity, electrical conductivity, reflectivity, grain size, coefficient of thermal expansion, brittleness, temperature tolerance, conductivity, and/or reduce grain size of the cladding.

In general, alloys suitable for the present invention may involve mixtures where one component is present at fractions as low as 0.0001%. In other instances, alloys with large fractions of more than one compound will be desirable. One embodiment of the ZMW uses aluminum as the cladding of the ZMW structure. As an example of how alloys can be beneficial to a ZMW structure, it is useful to consider different alloys of aluminum in how they would affect a ZMW. In the art of metalurgy, numerous materials are alloyed with aluminum. Non-limiting examples of materials suitable to alloy with aluminum are antimony, arsenic, beryllium, bismuth, boron, cadmium, calcium, carbon, cerium, chromium, cobalt, copper, gallium, hydrogen, indium, iron, lead, lithium, magnesium, manganese, mercury, molybdenum, nickel, niobium, phosphorous, silicon, vanadium, zinc and others. By way of example of how the introduction of another element could beneficially impact the ZMW performance, the introduction of boron to aluminum is known to increase the conductivity of aluminum. An increase in conductivity of the metal film may improve the performance by decreasing the penetration depth thereby decreasing the observation volume. A preferred embodiment includes an alloy of aluminum that is more than 0.0001% of a dopant. A more preferred embodiment includes an alloy of aluminum that is more than 0.005% of a dopant. A still more preferred embodiment includes an allow of aluminum that is more than 0.1% of a dopant.

In contrast, some materials are expected to decrease the performance of the ZMW structure, and in these instances it will be desirable to take measures to eliminate certain impurities. For example, in certain applications it may be desirable to decrease the amount of lead or arsenic if toxicity of the device is a concern. A preferred embodiment of the device includes a metal film that is less than 1% arsenic. A more preferred embodiment of the device includes a metal films that is less than 0.1% arsenic. A still more preferred embodiment includes a metal film that is less than 0.001% arsenic. A still more preferred embodiment includes a metal film that is less than 0.00001% arsenic. An additional preferred embodiment includes a metal film that is less than 1% lead. A still more preferred embodiment includes a metal film that is less than 0.1% lead. A still more preferred embodiment includes a metal film that is less than 0.01% lead. A still more preferred embodiment includes a metal film that is less than 0.001% lead. A still more preferred embodiment includes a film that is less than 0.00001% lead. In other applications where optical confinement performance is especially important, impurities that tend to reduce the conductivity, thereby worsening the confinement, will be undesirable. For example, vanadium is known in the art of metallurgy to reduce the conductivity of aluminum. A preferred embodiment includes a metal film that is less than 0.1% vanadium. A still more preferred embodiment includes a metal film that is less than 0.01% vanadium. A still more preferred embodiment includes a film that is less than 0.001% vanadium.

Semi-conducting materials suitable for fabricating the cladding are generally opaque, and they include silicon, silicates, silicon nitride, gallium phosphide, gallium arsenide, or any combinations thereof.

Figure 10:
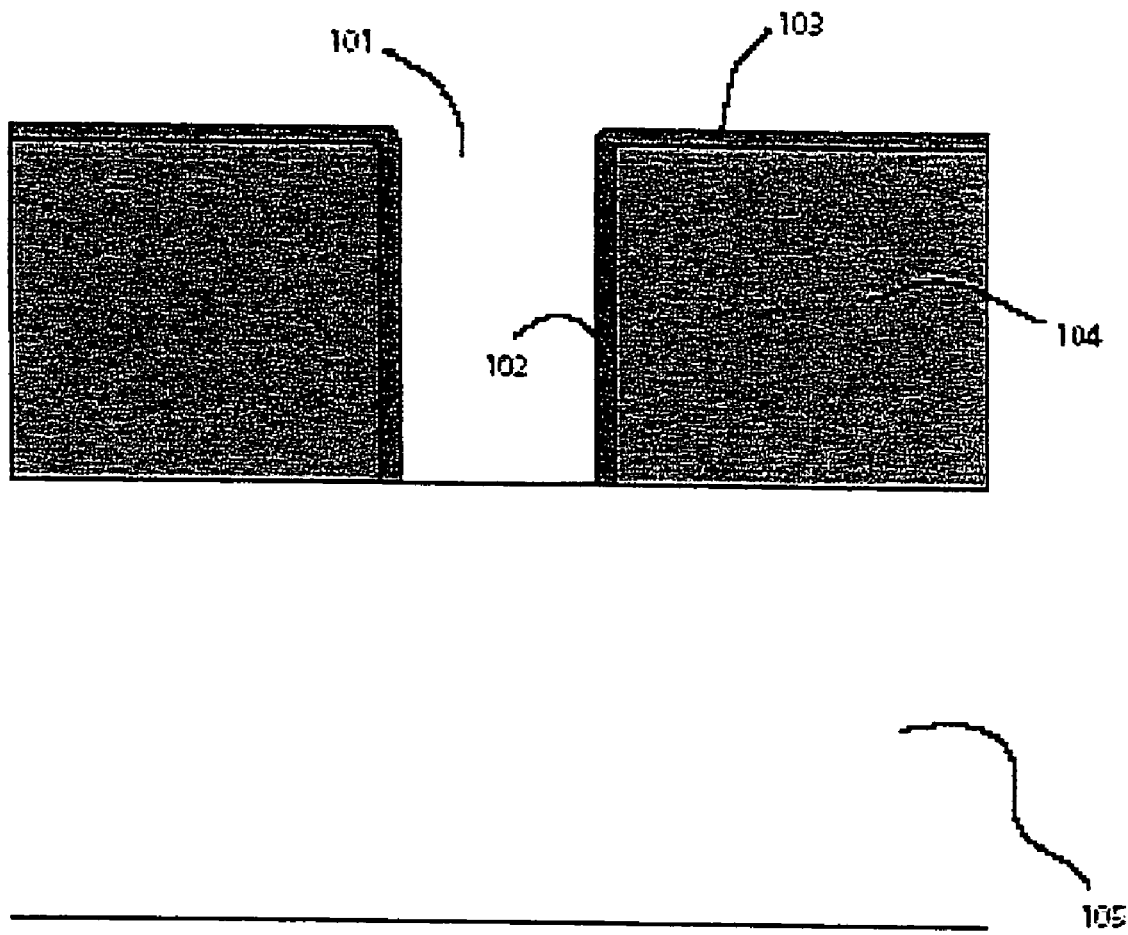
FIG. 10, depicts a coated ZMW 101 that is bound to a substrate 105. The ZMW comprises a sidewall 102, a coating 103 on the upper surface, and a metal film 104.

The cladding of the subject zero-mode waveguide may be coated with materials to improve the surface quality. For instance, coating may enhance the durability of the cladding material. In addition, coating is particularly desirable if the reactants contained in the core are prone to interact or adhere to the cladding material. A variety of appropriate coating materials are available in the art. Some of the materials may covalently adhere to the surface, others may attach to the surface via non-covalent interactions. Non-limiting examples of coating materials include aluminum oxide film, silanization reagent such as dimethychlorosilane, dimethydichlorosilane, hexamethyldisilazane or trimethylchlorosilane, polymaleimide, and siliconizing reagents such as silicon oxide, Aquasil™, and Surfasil™. An illustrative coated ZMW (101) is shown in FIG. 10. The ZMW (101) is bound to a substrate 105. The ZMW comprises a sidewall 102, a coating 103 on the upper surface, and a metal film 104.

In certain embodiments, it may be advantageous to construct the confinement from metal compositions that are inhomogeneous combinations of more than one material. For example, for certain applications, it may be beneficial to provide a composition that comprises more than one layer, each layer having a different composition, or composition that varies within a layer. This can have beneficial effects on several aspects of the performance of the confinement, including but not limited to the nature of the optical confinement, the structural strength and behavior of the device, the characteristics of the surface chemistry of the device or the like. In one embodiment the confinement comprises two layers in which one of the layers serves to enhance the adhesion of the second layer to a substrate. In another embodiment, the composition of the cladding film varies as a function of the axial position relative to the confinement, so as to provide different optical performance than would be obtained from a layer of uniform composition. In a particular version of this embodiment, the film comprises a composition that has a larger value of skin depth close to the surface of the substrate, and comprises a composition that has a smaller value of skin depth farther from the surface of the substrate, so that the nature of the confinement is to be more uniform in shape near the surface and then tapering off more quickly a larger distances away from the substrate. In another embodiment, the thicknesses of two different layers comprising the cladding of the confinement are chosen so that a specific optical condition is achieved at the substrate of the device, such as constructive or destructive interference.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda_c$). For a circular guide of diameter d and having a clad of perfect conductor, $\lambda_c$ is approximately 1.7×d. The cross sectional area of the core may be circular, elliptical, oval, conical, rectangular, triangular, polyhedral, or in any other shape. The various shapes can have particular suitability for certain applications. For instance, elongated cross-sections can be useful to provide enhanced access to molecules with mechanical persistence or stiffness, such as DNA. Cross sections ranging from extended slots to ovals of various aspect ratio will significant increase the accessibility of the persistent molecule to the detection zone of the structure, without excessive compromise in the axial attenuation of radiation. Although uniform cross sectional area is preferred, the cross sectional area may vary at any given depth of the guide if desired. Preferred average cross sectional areas range from 100 $nm^2$ to 10,000 $nm^2$.

In a preferred embodiment, the core is non-cylindrical. In one aspect of this embodiment, a non-cylindrical core comprises an opening on the upper surface and a base at the bottom surface that is entirely surrounded by the cladding, wherein the opening is narrower in lateral dimension than the base. This configuration significantly restricts the diffusion of reactants, and hence increases the average residence time in the observation volume. Such configuration is particularly useful for measuring the association rate constant (on-rate) of a chemical reaction. In another aspect, the core comprises an opening that is wider in lateral dimension than the base. Such configuration allows easier access to large molecules that impose a steric or entropic hindrance to entering the structure if the open end of the zero mode waveguide was as small as the base needed to be for optical performance reasons. Examples include the accessibility for long strand polyelectrolytes such as DNA molecules that are subject to entropic forces opposing entry into small openings.

The zero-mode waveguides embodied in the present invention have a relatively high fill fraction ratio, typically above 0.0001, preferably above 0.001, more preferably above 0.01, and even more preferably above 0.1. As used herein, "fill fraction" of a pattern refers to the ratio of the area occupied by the foreground of the pattern to the total area occupied by the pattern (foreground and background, together). The terms "fill fraction ratio" and "fill faction" are used interchangeably. In the context of zero-mode waveguide, the foreground is considered to be the area occupied by the core of the zero-mode waveguide, and the background is the area between the zero-mode waveguide (e.g., the aluminum film that forms the cladding in certain designs). The zero-mode waveguides with high fill fraction ratios are particularly useful for performing homogenous assays. The fill fraction can be calculated by summing the total areas of all of the zero-mode waveguides in the array and dividing by the total available area including both the zero-mode waveguides and the spaces between them. For example, if a zero-mode waveguide has a diameter of 50 nm, then the area of this zero-mode waveguide is one fourth of 7,850 square nanometers or 1962.5 $nm^2$. If these zero-mode waveguides are in a square array separated by 100 nm, the total available area is 10,000 square nanometers for each zero-mode waveguide. Therefore, the array has a fill fraction of one fourth of 78% or 19.6%, which would provide nearly four orders of magnitude higher signal strength in a surface binding assay than a zero-mode waveguide having a fill fraction on the order of 0.01%.

In a bioassay such as an ELISA or other molecular binding bioassay, one limitation is the inability to operate "homogeneously", or in a mode where solutions may be added to a mixture but nothing removed. This complicates highly multiplexed assays, as provisions for both adding and removing material from a large number of wells is significantly more complex than the provisions for simply adding materials. In the case of the ELISA assay, the removal of materials is necessary, because the fluorescent (or other) markers that remain free in solution at the end of the assay would interfere with the ability to detect markers bound to the reaction surface. Techniques to overcome this have been devised to exploit the short range of radioactive emissions from certain radioisotopes, but these techniques have inherent difficulties associated with personnel safety and waste disposal. Other methods for confining the sensitivity of the assay to the surface have been devised, such as total internal reflection confinement (TIR), and confocal detection. The zero-mode waveguide photonic structure allows a simpler and less expensive optical system configuration than either of these techniques, and vastly outperforms both from the perspective of confinement of sensitivity to the surface.

The fill fraction is important in bioassays, because the effective probe area is limited to the surface area of the bottoms of the zero-mode waveguide in the detection region. The amount of signal detectable in such an assay will be directly proportional to the available area, and having a larger fraction of the available surface occupied by zero-mode waveguides will thus increase the signal strength of measurements of such assays. A high fill fraction structure would be generally useful in any surface sensitivity application, not limited to the ELISA assay.

The cutoff wavelength is the wavelength above which the waveguide is essentially incapable of propagating electromagnetic energy along the waveguide under the illumination geometry used. Given the geometry of the core, and the properties of the cladding material, as well as the wavelength of the incident electromagnetic radiation, one skilled in the art can readily derive the cutoff wavelength by solving the Maxwell's equations (see, e.g., John D. Jackson, CLASSICAL ELECTRODYNAMICS, second edition, John Willey and Sons). The choice of the incident wavelength will depend on the particular application in which the subject array is to be employed. In certain aspects, the incident wavelength may be selected from a range of about 10 nm to about 1 mm. For detecting fluorescent signals, the incident wavelength is typically selected from the range of about 380 nm to about 800 nm. Polarized (linearly or preferably circularly polarized) or unpolarized incident radiation is generally employed to illuminate the array in order to create a desired observation volume.

In a separate embodiment, the present invention provides an alternative optical confinement termed external reflection confinement (ERC). In contrast to the conventional total internal reflection confinement (IRC), the low index medium is the electromagnetic radiation carrier, and the high index (and opaque) medium is the reflector. As such, the roles of the refractive indices are reversed as compared to the IRC situation. ERC generally requires some kind of means to provide the analyte (i.e., the molecules under investigation) in the opaque phase.

IRC relies on reflection of an electromagnetic radiation incident on an interface between high index of refraction and low index of refraction. When light is incident above the critical angle of total internal reflection (known in the art), all of the incident electromagnetic radiation is reflected and none is transmitted into the low index phase. A thin region of evanescent radiation is established proximal to the interface on the low index side. This radiation field is typically an exponentially decaying field with an attenuation length in the range from about 100 nm to about 200 nm, depending on the angle of incidence and the indices of refraction of the two phases. If the low index phase is a solution containing an analyte, then the evanescent radiation can be used to probe the analyte in the solution with a high degree of surface sensitivity.

In ERC, the carrier of the propagating electromagnetic radiation is a transparent low index film, and the analyte-bearing medium is a high-index metallic opaque film. In this case, most of the radiation is reflected irrespective of the angle of incidence, and non-reflected light is rapidly attenuated according to the skin depth of the metal. Typically, means is provided to convey the analyte within the metal phase. Theses means can take the form of a nanocapillary tube constructed within the metal layer. When sufficiently small, the presence of such a tube will have little effect on the distribution of energy in the two media, but can be amply large enough to convey biomolecules. To be small enough, any defects in the metal film must be small compared with the wavelength of the illumination. This can be achieved because of the large ratio between the wavelength of visible light, and the typical size of biomolecules of interest. While visible light is typically between 400 nm and 750 nm in wavelength, biomolecules of interest are generally in the vicinity of 1-30 nm in diameter. The attenuation of the radiation at the interface can be used to confine illumination to a very small region of the analyte. A small hole in an index matched (to water) film on a high index substrate could provide lateral confinement beyond what is possible with diffraction limited optics in the TIR context. This could give 100 zeptoliter confinement in principle. In this method, a version of total internal reflection confinement is used in which a solid material index-matched to the analyte solution is applied to the substrate surface and then perforated with nanoscale holes. When used in TIR mode, these structures will provide additional confinements above what can be obtained with TIR alone.

Other alternative confinements are index matching solids. As an illustrative example, such optical confinement can be fabricated starting with a high index transparent susbtrate such as sapphire, spin coat 200 nm of PMMA (polymethyl methacrylate) resist resin. Exposure to electron beam lithography will render isolated spots soluble according to the pattern applied. After development, the device will have nano-scale holes in the PMMA layer and are ready to be used in a TIR setup. Axial confinement is unaffected by the PMMA layer, as it has nearly the same index of refraction as the solution containing the analyte, but the solution is physically prevented from approaching near the surface except where the holes are situated, providing a degree of lateral confinement given by the diameter of the holes.

The optical confinements can be provided with an optical system capable of detecting and/or monitoring interactions between reactants at the single-molecule level. Such optical system achieves these functions by first generating and transmitting an incident wavelength to the reactants contained in the confinements, followed by collecting and analyzing the optical signals from the reactants. Such systems typically employ an optical train that directs signals from an array of confinements onto different locations of an array-based detector to simultaneously detect multiple different optical signals from each of multiple different confinements. In particular, the optical trains typically include optical gratings or wedge prisms to simultaneously direct and separate signals having differing spectral characteristics from each confinement in an array to different locations on an array based detector, e.g., a CCD. By separately directing signals from each confinement to different locations on a detector, and additionally separating the component signals from each confinement to separate locations, one can simultaneously monitor multiple confinements, and multiple signals from each confinement.

The optical system applicable for the present invention comprises at least two elements, namely an excitation source and a photon detector. The excitation source generates and transmits incident light used to optically excite the reactants contained in the optical confinement. Depending on the intended application, the source of the incident light can be a laser, laser diode, a light-emitting diode (LED), a ultraviolet light bulb, and/or a white light source. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously. A wide variety of photon detectors are available in the art. Representative detectors include but are not limited to optical reader, high-efficiency photon detection system, photodiode (e.g. avalanche photo diodes (APD)), camera, charge couple device (CCD), electron-multiplying charge-coupled device (EMCCD), intensified charge coupled device (ICCD), and confocal microscope equipped with any of the foregoing detectors. Where desired, the subject arrays of optical confinements contain various alignment aides or keys to facilitate a proper spatial placement of the optical confinement and the excitation sources, the photon detectors, or the optical transmission element as described below.

The subject optical system may also include an optical transmission element whose function can be manifold. First, it collects and/or directs the incident wavelength to the optical confinement containing the reactants.

Second, it transmits and/or directs the optical signals emitted from the reactants inside the optical confinement to the photon detector. Third, it may select and/or modify the optical properties of the incident wavelengths or the emitted wavelengths from the reactants. Illustrative examples of such element are diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements. For instance, a planar waveguides can be operatively coupled to an array of zero-mode waveguides to directly channel incident wavelengths to the respective cores of the zero-mode waveguides so as to minimize the loss of wave energy. The planar channel can be included as a detachable unit located at the base of array substrate, or it can be bonded to the substrate as an integral part of the array.

The optical transmission element suitable for use in the present invention encompasses a variety of optical devices that channel light from one location to another in either an altered or unaltered state. Non-limiting examples of such optical transmission devices include optical fibers, diffraction gratings, arrayed waveguide gratings (AWG), optical switches, mirrors, (including dichroic mirrors), lenses (including microlens and nanolens), collimators, filters, prisms, and any other devices that guide the transmission of light through proper refractive indices and geometries.

In a preferred embodiment, the optical confinement of the present invention is operatively coupled to a photon detector. For instance, the arrayed optical confinement is operatively coupled to a respective and separate photon detector. The confinement and the respective detector can be spatially aligned (e.g., 1:1 mapping) to permit an efficient collection of optical signals from the waveguide. A particularly preferred setup comprises an array of zero-mode waveguides, wherein each of the individual waveguides is operatively coupled to a respective microlens or a nanolens, preferably spatially aligned to optimize the signal collection efficiency.

Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement.

Figure 7:
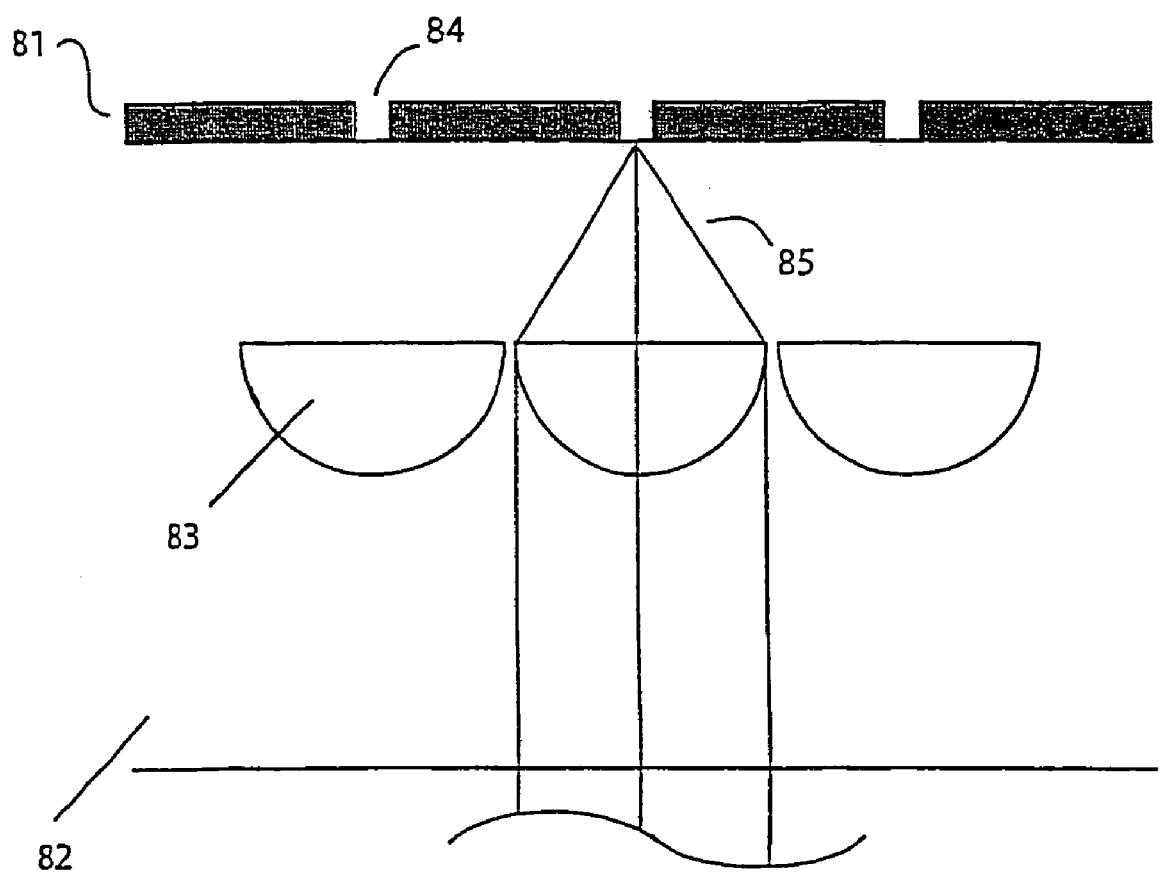
FIG. 7 illustrates an array of ZMWs optically linked to an optical system.

An exemplary optical setup is shown in FIG. 7, in which an array of ZMWs is optically linked to an optical system. This system comprises a ZMW array film (81), a glass cover slip (82) through which light transmits and further converges through set of integral lenses (83) made of a material having a different index of refraction than that of the glass. In particular, 84 shows a ZMW structure, 85 indicates a ray of light being focused onto the ZMW by the integral lenses such as the embedded microlens.

Figure 11:
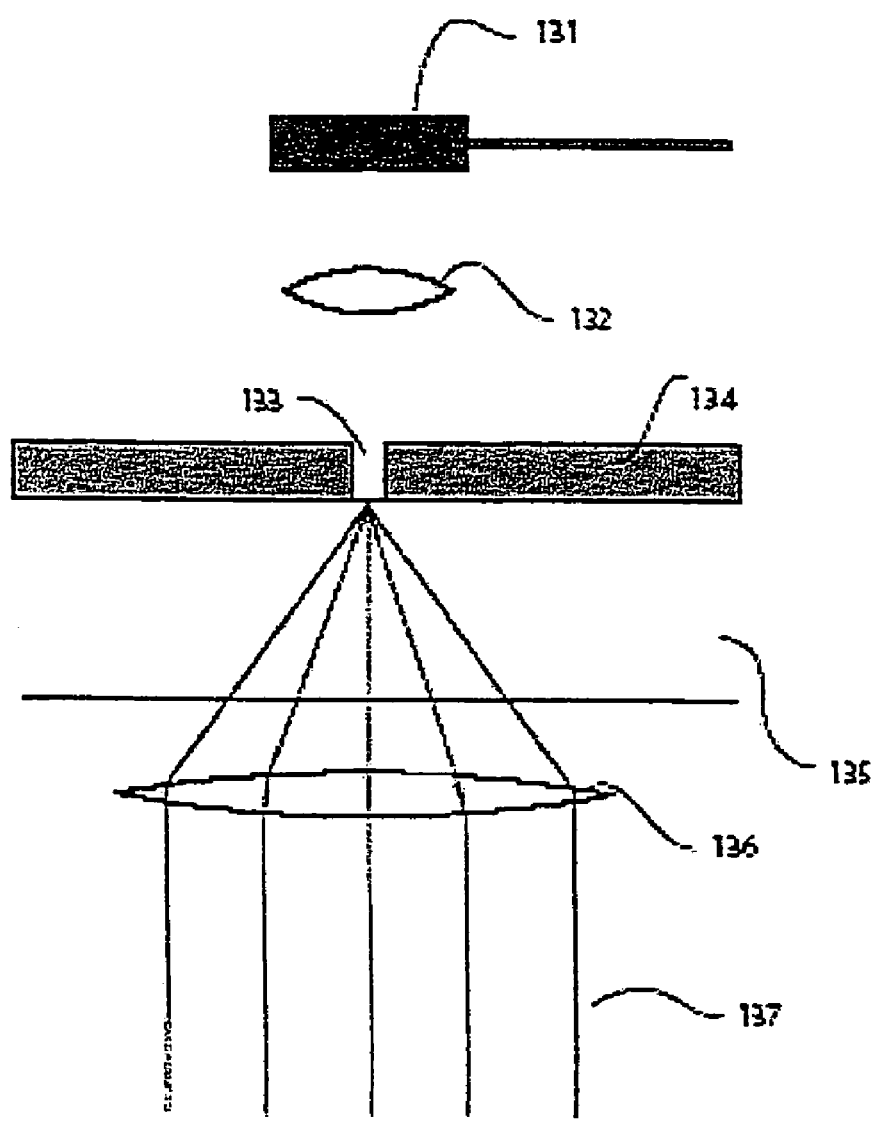
FIG. 11 depicts one alignment strategy and optical setup.
Figure 12:
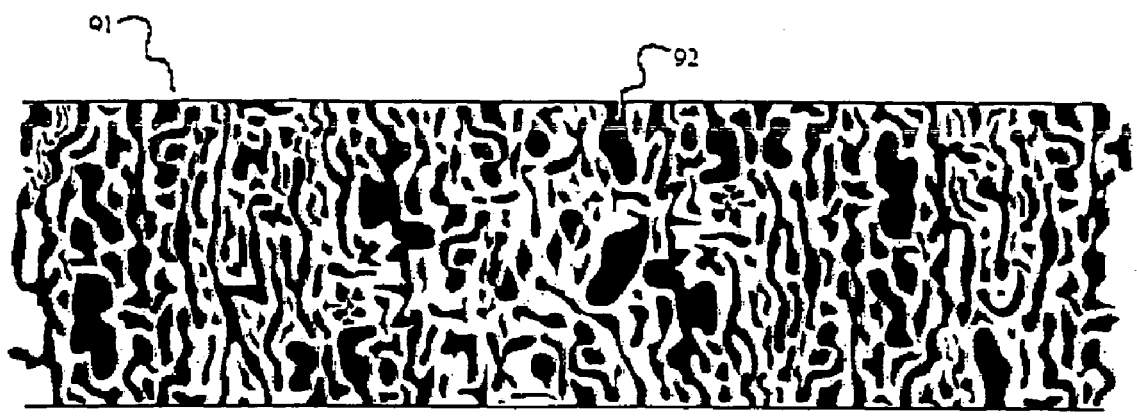
FIG. 12 depicts an alternative optical confinement made of porous film 91 on a substrate 93. 92 represents the pores in the film.
Figure 13A:
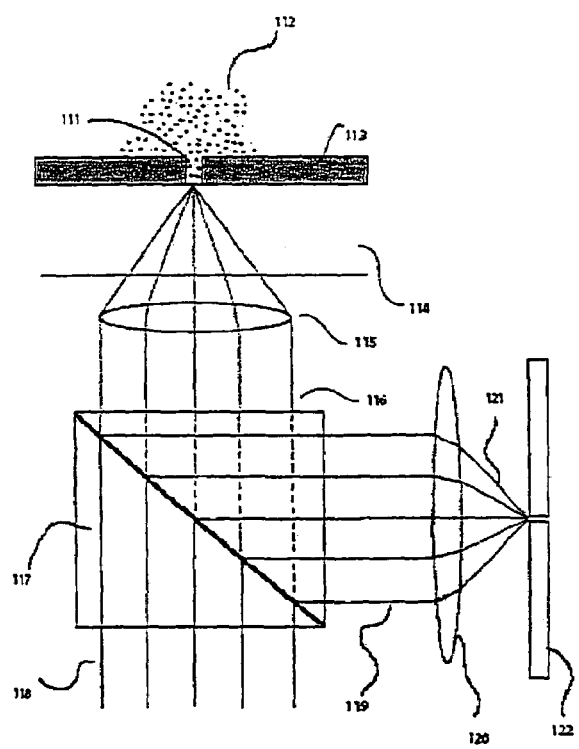
FIGS. 13A-B depict an alignment detection system and the associated components.
Figure 13B:
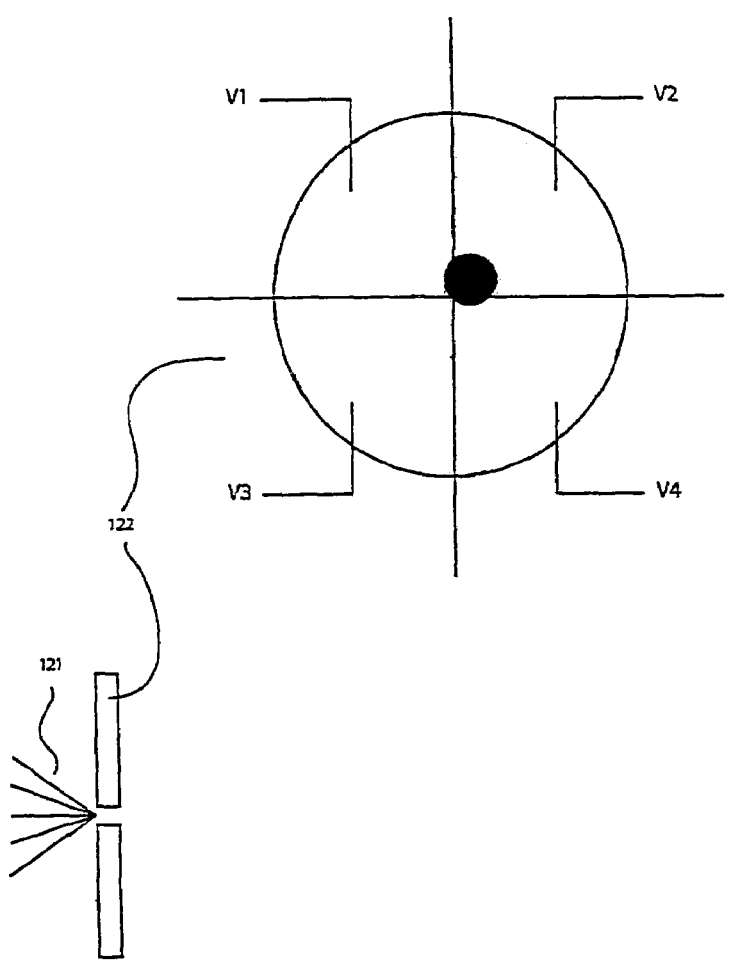

FIG. 11 depicts one alignment strategy and optical system. The system comprises a photodetector 131, an optional lens 132 for collecting light, a ZMW 133 having a metal film 134 coupled to a substrate 135, and an objective lens 136 that is aligned with the incident light beam 137. FIG. 13 depicts an exemplary alignment detection system and the associated components. The illustrative system 13A comprises an optical confinement such as a zero-mode waveguide 111 having a metal film 113 coupled to a substrate 114. The zero-mode waveguide 111 typically contains signal generating molecules 112, and is optically linked to the associated components including an objective lens 115, a beam splitter/dichroic cube 117, optically a telen lens 120 (used in infinity corrected systems), and a photodetector 122 (e.g., a quadrant photodetector). 116 depicts rays propagating though system. 118 depicts the incident illumination rays. 119 depicts the return rays moving towards the detector 122. FIG. 13B depicts a front view of the quadrant photodiode. Shown in the center of the figure is a beam misaligned on the center of the quadrant detector. The four voltages generated by the four quadrants can be processed to determine the degree and direction of mis-alignment of the beam and thus the optical confinement such as ZMW 111.

The subject arrays may comprise a single row or a plurality of rows of optical confinements on the surface of a substrate, where a plurality of lanes are present, for example, usually at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter or multi-well plate wherein each micro well of the plate contains a subject array of optical confinements. Typically, such multi-well plates comprise multiple reaction vessels or wells, e.g., in a 48 well, 96 well, 384 well or 1536 well format. In such cases, the wells are typically disposed on 18 mm, 9 mm, 4.5 mm, or 2.25 mm centers, respectively.

Figure 4:
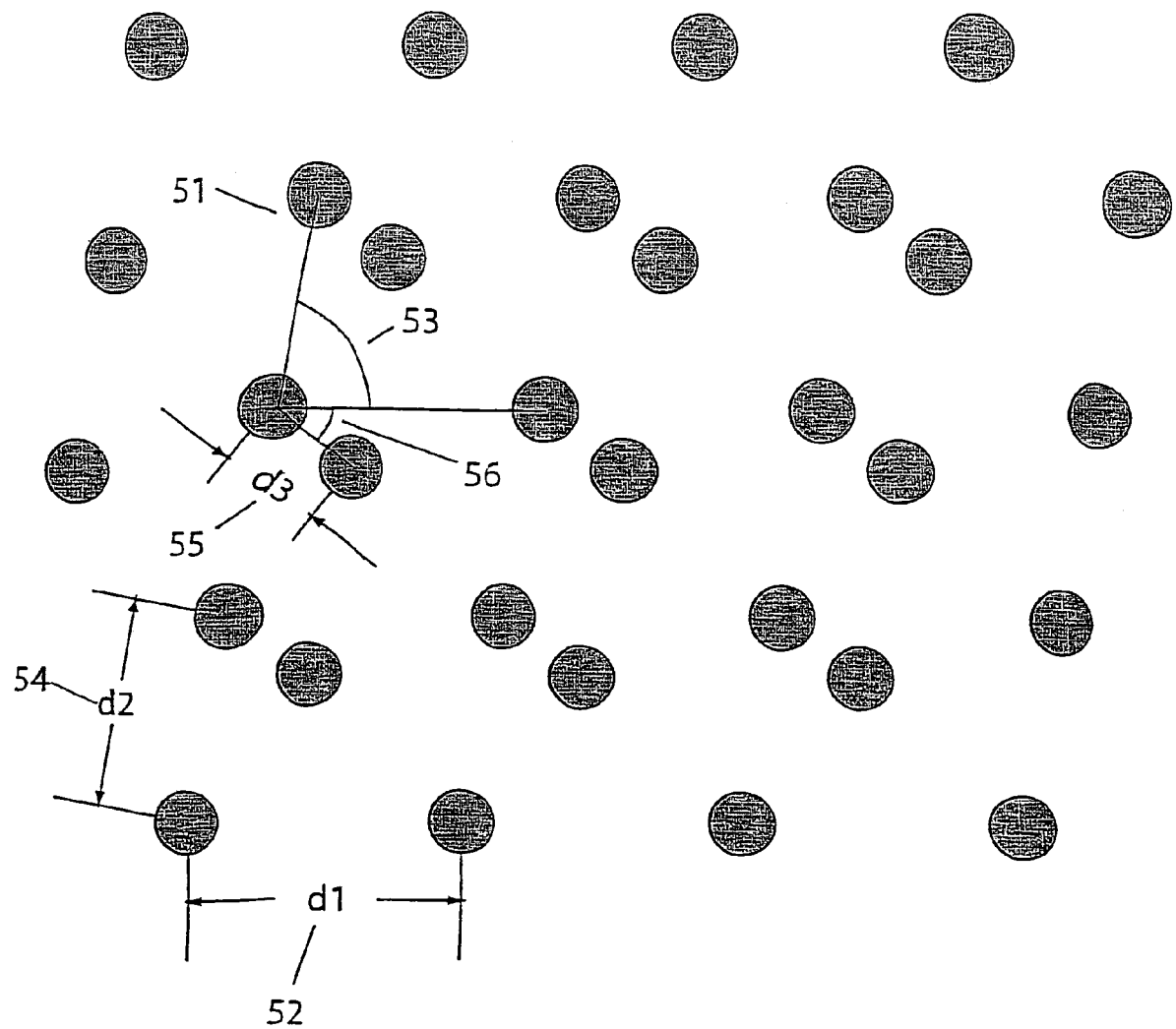
FIG. 4 depicts a top view of an illustrative regular disposition of ZMWs.
Figure 5:
FIG. 5 depicts an array of arrays, in which a subarray 71 is part of a super array 72.
Figure 5:

An illustrative array of arrays is depicted in FIG. 5 in which a subarray 71 is part of a super array 72. Arrays can also be arranged in lattices. For example, FIG. 4 depicts a top view of an illustrative regular disposition of ZMWs. In this configuration, there is a lattice defined by the parameters d1, d2, and the angle 53. In addition to a ZMW at each lattice point, there is a complex unit cell that comprises a plurality of ZMWs in an arrangement that is defined by a list of angles and distances with one angle and one distance for each element of the unit cell. In particular, 52 represents the first lattice distance, 53 represents the lattice angle, 54 represents the second lattice distance, 55 represents the unit cell first distance, and 56 represents unit cell first angle. While this figure shows an array with a unit cell of two components, the unit cell can have any plurality of elements.

As described above, the subject arrays comprise a plurality of optical confinements. In some embodiments, the arrays have at least about $20 \times 10^4$ distinct optical confinements, preferably at least about $20 \times 10^6$ distinct confinements, and more preferably at least about $20 \times 10^8$ confinements. The density of the spots on the solid surface in certain embodiments is at least above $4 \times 10^4$ confinements per mm$^2$, and usually at least about $8 \times 10^4$, at least about $1.2 \times 10^5$, or at least about $4 \times 10^6$ confinements per mm$^2$, but does not exceed $4 \times 10^{12}$ confinements per mm$^2$, and usually does not exceed about $4 \times 10^{10}$ confinements per mm$^2$. The overall size of the array generally ranges from a few nanometers to a few millimeters in thickness, and from a few millimeters to 50 centimeters in width or length. Preferred arrays have an overall size of about few hundred microns in thickness and may have any width or length depending on the number of optical confinements desired.

Figure 2:
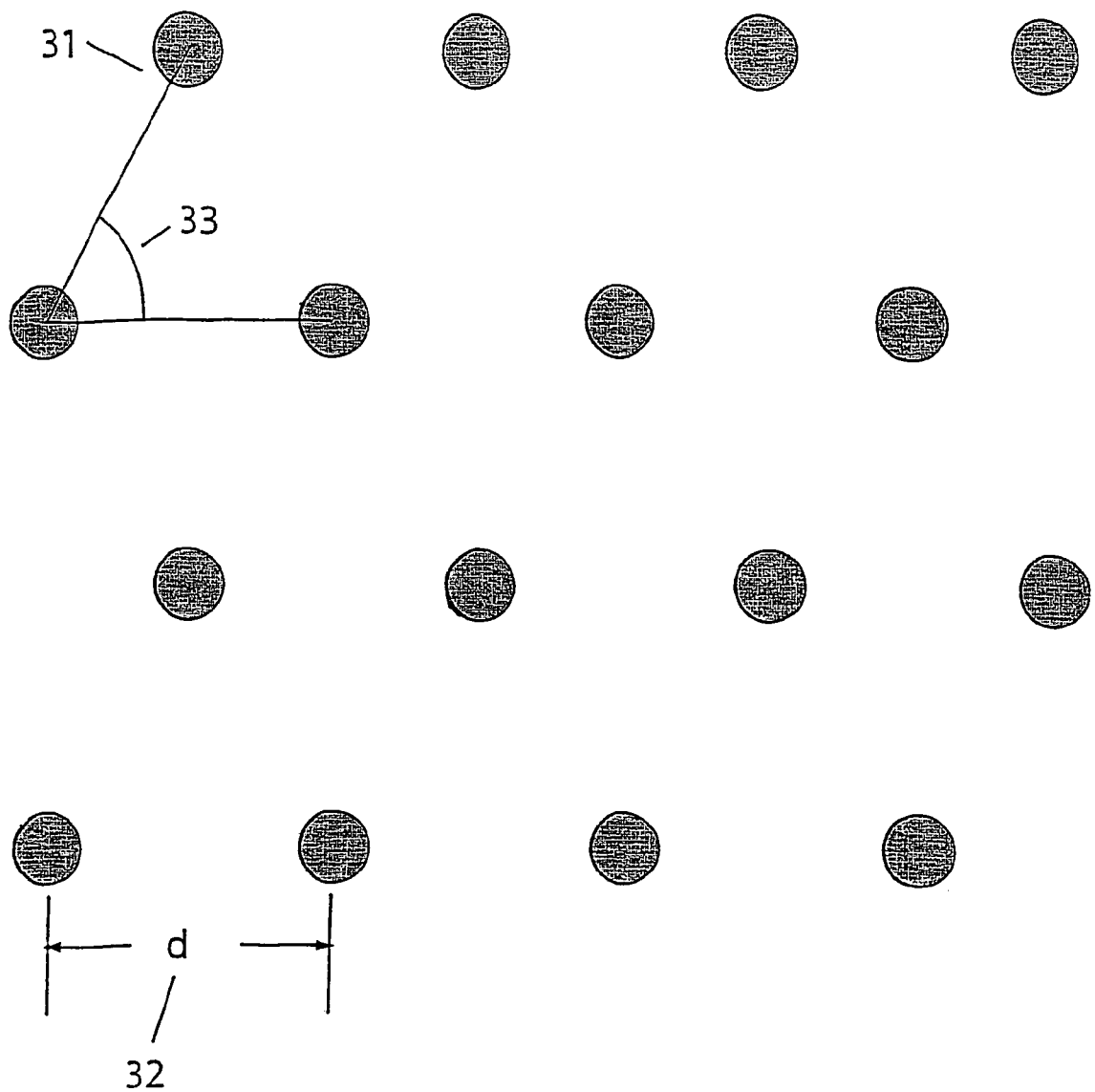
FIG. 2 depicts a top view of an array of illustrative optical confinements, here zero-mode waveguides arranged in a non-square format.
Figure 3:
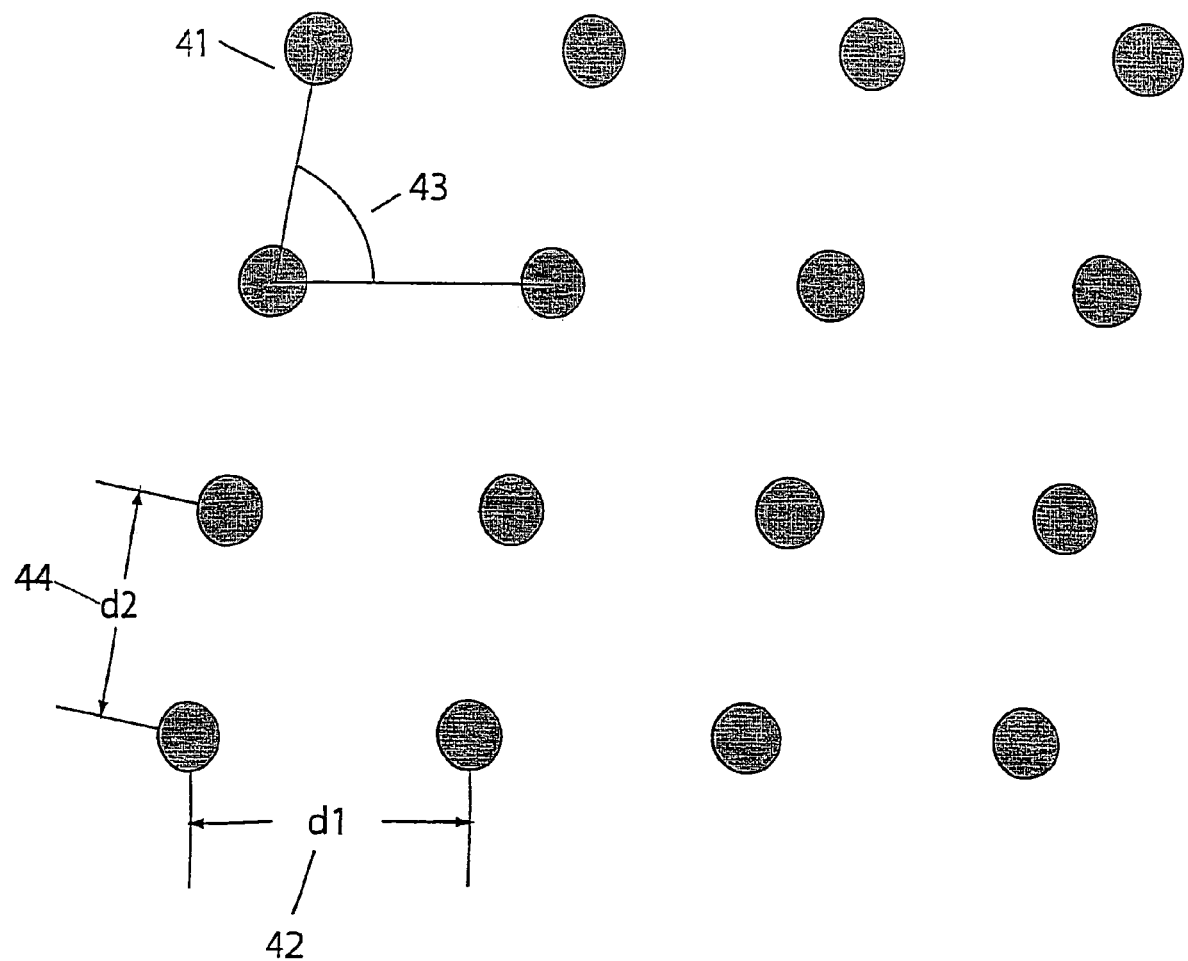
FIG. 3 depicts a top view of an illustrative 2-dimentional array with an illustrative angle and two different unit vector lengths.

In one example as shown in FIG. 1, the array of optical confinements, e.g. zero-mode waveguides, are arranged in a square format. The array comprises a representative zero-mode waveguide 21, separated from an adjacent waveguide by a distance "d" (22 represents the inter-zero mode waveguide spacing). In another example as shown in FIG. 2, the array of optical confinements, e.g. zero-mode waveguides, are arranged in a non-square format. The array comprises a representative zero-mode waveguide 31, separated from an adjacent waveguide by a distance "d" (32 represents the inter-zero mode waveguide spacing). 33 shows the angle formed between any three adjacent ZMWs (e.g., 60 degrees). FIG. 3 depicts a top view of another illustrative 2-dimentional array. The adjacent optical confinements are separated in one dimension by a distance of "d1" and in another dimension by a distance of "d2", with a unit vector angle 43.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements are typically placed close to each other relative to the incident wavelength.

Accordingly, in one aspect, the present invention provides an array of zero-mode waveguides comprising at least a first and at least a second zero-mode waveguide, wherein the first zero-mode waveguide is separated from the second zero-mode waveguide by a distance such that upon illumination with an incident wavelength, intensity of diffractive scattering observed from the first zero-mode waveguide at a given angle is less than that if the first zero-mode waveguide were illuminated with the same incident wavelength in the absence of the second zero-mode waveguide. Diffractive scattering can be reduced or significantly eliminated if an array comprises zero-mode waveguides spaced in a regular spaced lattice where the separation of zero-mode waveguides from their nearest neighbors is less than half the wavelength of the incident wavelength. In this regime, the structure behaves as a zero-order grating. Such gratings are incapable of scattering incident light despite having a large number of elements that by themselves would scatter very effectively. This arrangement is highly desirable for illumination approaches such as dark field illumination, where surface scattering would cause excitation radiation to be collected by the objective lens, thus increasing background noise. Useful wavelengths for illumination range from 250 nm up to 8 microns, meaning that an array of zero-mode waveguides with a spacing of less than 4000 nm would still be useful for application in this manner. A spacing of less than 2000 nm is more preferable, while a spacing of less than 1000 nm is even more preferable in this respect. Some configurations with spacing larger than one half of the wavelength can have the same advantage if the illumination is applied asymmetrically, or if the collection cone angle is configured to be less than 90 degrees. In addition to the benefit of reduced diffractive scattering, narrow spacing between the individual confinements decreases the illumination area and thus lowers the power demand.

Arrays having the optical confinements spaced far apart relative to the incident wavelength also have desirable properties. While the angle-dependent scattering raises the background signal that could be disadvantageous for certain applications, it provides a means particularly suited for characterizing the size and shape of the optical confinements. It also readily permits ensemble bulk measurements of molecule interactions, involving especially unlabelled molecules. Arrays suited for such applications generally contain individual confinements separated by more than one wavelength of the incident radiation, usually more than 1.5 times the incident wavelength, but usually does not exceed 150 times the incident wavelength.

Kits:

The present invention also encompasses kits containing the optical confinement arrays of this invention. Kits embodied by this invention include those that allow characterizing molecules and/or monitoring chemical reactions at a single-molecule level. Each kit usually comprises the devices and reagents which render such characterization and/or monitoring procedure possible. Depending on the intended use of the kit, the contents and packaging of the kit will differ. Where the kit is for DNA sequencing, the kit typically comprises: (a) an array of optical confinements, preferably zero-mode waveguides of the present invention, that permits resolution of individual molecules or the reaction of individual molecules, such as those that are present at a concentration higher than about 1 micromolar; (b) sequencing reagents typically including polymerases, aqueous buffers, salts, primers, and nucleotides or nucleotide analogs. Where desired a, 'control' nucleic acids of known sequence can be included to monitor the accuracy or progress of the reaction.

The reagents can be supplied in a solid form, immobilized form, and/or dissolved/suspended in a liquid buffer suitable for inventory storage, and later for exchange or addition into the reaction medium when the test is performed. Suitable individual packaging is normally provided. The kit can optionally provide additional components that are useful in the procedure. These optional components include, but are not limited to, buffers, capture reagents, developing reagents, labels, reacting surfaces, control samples, instructions, and interpretive information. Diagnostic or prognostic procedures using the kits of this invention can be performed by clinical laboratories, experimental laboratories, practitioners, or private individuals.

Preparation of the Optical Confinements:

The array of the present invention can be manufactured using nanofabrication techniques provided by the present invention, as well as those known in the fields of Integrated Circuit (IC) and Micro-Electro-Mechanical System (MEMS). The fabrication process typically proceeds with selecting an array substrate, followed by using appropriate IC processing methods and/or MEMS micromachining techniques to construct and integrate the optical confinement and other associated components.

Array Substrate:

In some embodiments, the array of optical confinements is present on a rigid substrate. In other embodiments concerning, e.g., porous films with reflective index media, flexible materials can be employed. In general, a rigid support does not readily bend. Examples of solid materials which are not rigid supports with respect to the present invention include membranes, flexible metal or plastic films, and the like. As such, the rigid substrates of the subject arrays are sufficient to provide physical support and structure to optical confinements present thereon or therein under the assay conditions in which the array is employed, particularly under high throughput handling conditions.

The substrates upon which the subject patterns of arrays are disposed, may take a variety of configurations ranging from simple to complex, depending on the intended use of the array. Thus, the substrate could have an overall slide or plate configuration, such as a rectangular or disc configuration, where an overall rectangular configuration, as found in standard microtiter plates and microscope slides, is preferred. Generally, the thickness of the rigid substrates will be at least about 0.01 mm and may be as great as 1 cm or more, but will usually not exceed about 5 cm. Both the length and the width of rigid substrate will vary depending on the size of the array of optical confinements that are to be fabricated thereon or therein.

The substrates of the subject arrays may be fabricated from a variety of materials. The materials from which the substrate is fabricated is preferably transparent to visible and/or UV light. Suitable materials include glass, semiconductors (e.g., silicate, silicon, silicates, silicon nitride, silicon dioxide, quartz, fused silica, and gallium arsenide), plastics, and other organic polymeric materials. In preferred aspects, silica based substrates like glass, quartz and fused silica are used as the underlying transparent substrate material.

The substrate of the subject arrays comprise at least one surface on which a pattern of optical confinements is present, where the surface may be smooth or substantially planar, or have irregularities, such as depressions or elevations. The surface may be modified with one or more different layers of compounds that serve to modulate the properties of the surface in a desirable manner. Modification layers of interest include: inorganic and organic layers such as metals, metal oxides, polymers, small organic molecules, functional moieties such as avidin/biotin and the like. The choice of methods for applying the coating materials will depend on the type of coating materials that is used. In general, coating is carried out by directly applying the materials to the zero-mode waveguide followed by washing the excessive unbound coating material from the surface. Alternatively or additionally, coating materials may be deposited using other conventional techniques, such as chemical vapor deposition (CVD), sputtering, spin coating, in situ synthesis, and the like. Certain coating materials can be cross-linked to the surface via heating, radiation, and/or by chemical reactions. In preferred aspects, suitable coating materials are coupled to substrate surfaces either covalently or through ionic or hydrophobic/hydrophilic interactions. In the case of silica based substrates, for example, silane chemistries are particularly suited for covalently attaching coating materials to surfaces, e.g., coupling groups, specific binding moieties, and the like. Such chemistries are well known to those of ordinary skill in the art and can be practiced without undue experimentation.

Fabrication Process:

Fabrication of the subject array substrates can be performed according to the methods described as follows or other standard techniques of IC-processing and/or MEMS micromachining. The standard techniques known in the art include but are not limited to electron-beam lithography, photolithography, chemical vapor or physical vapor deposition, dry or wet etching, ion implantation, plasma etching, bonding, and electroplating. Additional fabrication processes are detailed in the U.S. Patent Application Publication No. 2003/0174992, the content of which is incorporated by reference in its entirety.

In a preferred embodiment, the present invention provides a negative tone fabrication process, which provides for the creation of optical confinements having more uniform and consistent dimensions than conventional positive tone fabrication processes that can yield optical confinements of varying dimensions. A comparison of the two fabrication processes is shown in Table 1 below.

TABLE 1

Positive and Negative Tone Process Steps in Fabrication of Zero-Mode Waveguides

| Step # | Positive Tone Process | Negative Tone Process |
|---|---|---|
| 1 | Clean fused silica substrates in heated solution of hydrogen peroxide and ammonium hydroxide. | Same |
| 2 | Cascade rinse substrates in deionized water. | Same |
| 3 | Clean substrates in oxygen plasma cleaner. | Same |
| 4 | Coat substrates with metal film by either thermal evaporation or sputtering. | Spin-coat substrates with electron-beam resist. |
| 5 | Spin-coat substrates with electron-beam resist over the metal layer. | Bake casting solvent out of film. |
| 6 | Bake casting solvent out of film. | Expose resist with electron beam lithography. |
| 7 | Expose resist with electron beam lithography. | Develop resist in chemical bath to reveal array of small pillars with large empty gaps in resist. |

TABLE 1-continued

Positive and Negative Tone Process Steps in Fabrication of Zero-Mode Waveguides

| Step # | Positive Tone Process | Negative Tone Process |
|---|---|---|
| 8 | Develop resist in chemical bath to reveal holes. | Rinse developer away and dry chips. |
| 9 | Rinse developer away and dry chips. | Coat chips with metal film by either thermal evaporation or sputtering. |
| 10 | Use reactive-ion etching to transfer resist pattern into metal film. | Dissolving underlying negative resist using Microposit 1165 Stripper. |
| 11 | Strip resist using oxygen plasma. | Same |

In a negative tone process, a negative resist is applied to the substrate. A resist is negative if it is rendered insoluble by application of some agent, wherein the case of photoresists or e-beam resists, the agent is optical energy or electron beam energy, respectively. Alternatively, a positive tone resist can be used with a negative pattern. A negative tone pattern is characterized by the application of the agent in all areas except the location of the optical confinement, e.g., zero-mode waveguide, contrasted with a positive tone image in which the agent is confined only to the optical confinement area. In either case, after development of the resist, resist remains only in the areas where the optical confinement is intended to lie. It is useful in many cases to use means to achieve an undercut sidewall profile of these remaining resist features. Many techniques exist in the art to obtain undercut sidewalls, for example, in electron beam lithography. For instance, when using negative tone resists, one method is to apply to layers of electron beam resist to the surface sequentially, the upper film having a higher sensitivity to the energy delivered to it by the electron beam. Because the beam has a tendency to spread, a larger area of the upper film will be rendered insoluble than in the lower layer, resulting in an overhang beneath the upper layer as desired.

After development and appropriate cleaning procedures known in the art such as a plasma cleaning procedure, the metal film comprising the optical confinement can be applied by one of several methods, including metal evaporation, molecular beam epitaxy and others. In the case that the resist profile is undercut as discussed above, the metal that is deposited in the regions still occupied by the resist will rest on top of the resist rather than resting on the device surface. The resist layer is subsequently removed by any of several techniques including solvent dissolution either with or without ultrasonication or other mechanical agitation, reactive plasma etching, vaporization or others. The metal which rested on the resist features is removed as the resist is removed ("lifted off"), while the resist resting directly on the substrate remains to form the walls of the optical confinement.

The advantage of this process is that the size of the optical confinement is determined by the size of the resist feature, and does not rely on the fidelity of reactive ion etch pattern transfer mechanisms, which can be highly variable for metal films, especially aluminum a desirable metal for these devices. The positive tone process is subject to the inherent variation in resist feature sizes plus the variation due to pattern transfer, while the negative tone process is subject to the first variability but not the second. Metal thin film techniques suffer from much less lateral variation, and so the overall accuracy is better. This method also does not rely on the availability of a suitable etch for the metal in question, allowing the application of the process to a much wider selection of metals than the positive tone process.

Figure 6:
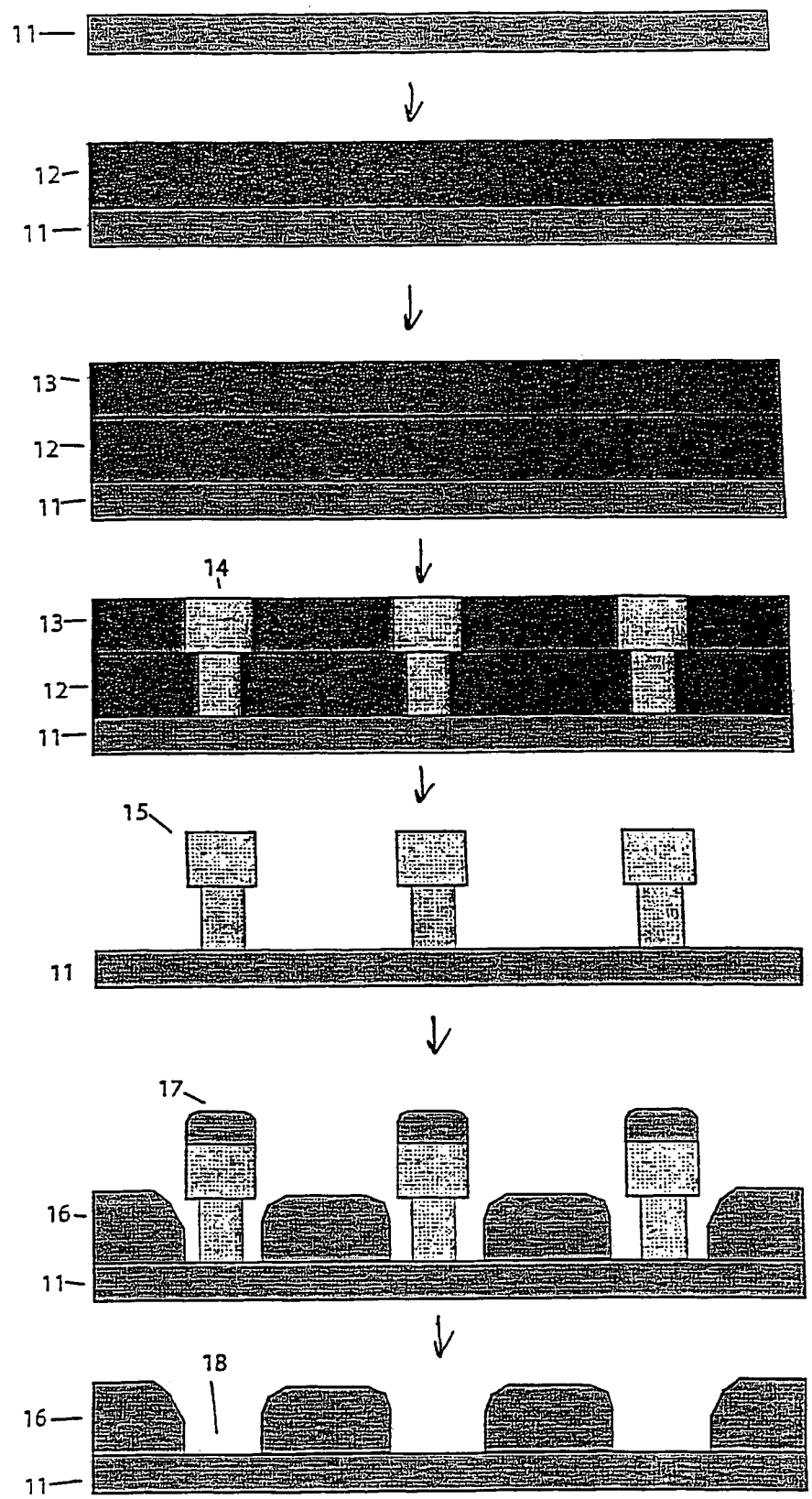
FIG. 6 illustrates a process of negative tone fabrication.
Figure 8:
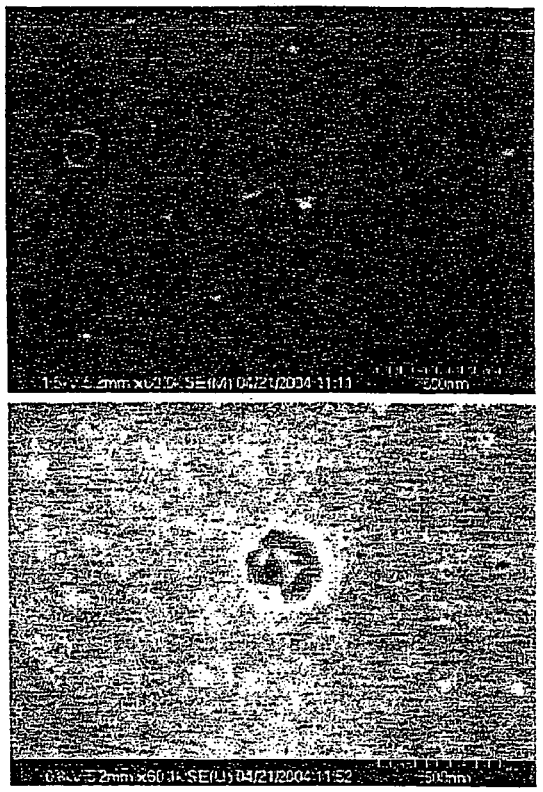
FIG. 8 depicts a scanning electron micrographs of ZMW structures fabricated by positive tone resist (left panels) or negative tone resist (right panels). The grain structure of the polycrystalline film is visible in the image as flecks, and the ZMWs as dark round structures.
Figure 8:
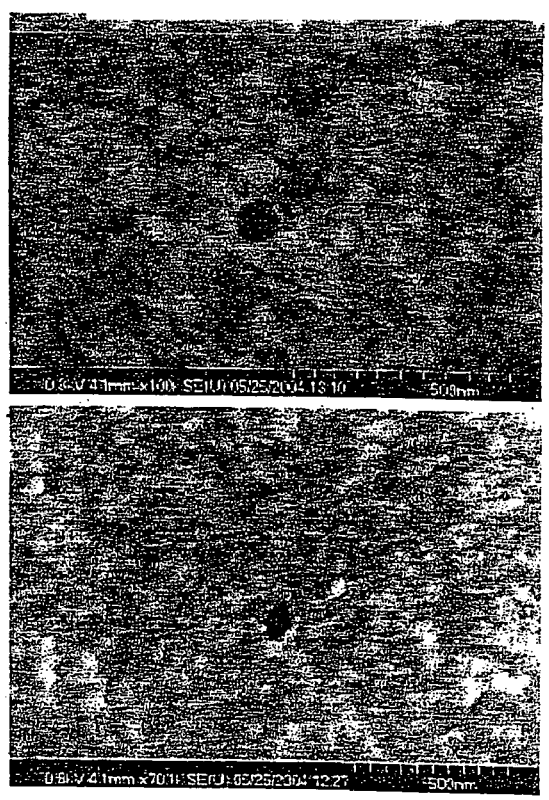

FIG. 6 is a schematic presentation of an illustrative negative tone process to make zero-mode waveguides. In this process, the substrate 11 is first coated with a layer of negative resist 12. Optionally, the substrate can be coated with a second resist layer 13. Exposure of the resist to the same pattern electron beam lithography tool used in the positive tone process, generates the opposite pattern as previously observed, namely one of a periodic array of small pillars of remaining resist, and empty gaps between the pillars 15. The final zero-mode waveguide structures are created by coating this pattern with a thin metal layer such as an aluminum layer 17, and then dissolving the underlying negative resist pillars 18. Because this process is not dependent on the thickness of the alumina layer or the crystal structure or morphology of the metal film, it produces a far more consistent configuration, and provides much finer control over the critical feature size. FIG. 8 depicts a scanning electron micrographs of ZMW structures fabricated by positive tone resist (left panels) or negative tone resist (right panels). The grain structure of the polycrystalline film is visible in the image as flecks, and the ZMWs as dark round structures.

A variant negative tone process is termed nanocasting. The steps of nanocasting are similar except that the use of bi-layer resist is avoided. The process first involves depositing on the surface of a substrate (in this case a single-layer resist would be used). The electron beam exposure and development follow, leaving a cylindrical feature for each dot in the exposure pattern. For this process, it is desirable to allow the metal deposition technique to apply material not just on the top of the resist structure but also on the sidewalls of the resist feature. This process is inherently three dimensional, in that a negative replica of the exterior surface of the three-dimensional resist feature is reproduced in the interior surface of the metal films that forms the optical confinement walls. In this case, the undercut resist profile and the various methods used to produce this are not necessary, as in the negative tone process, they are used specifically to prevent contact of the deposited film with the sides of the resist feature. In the nanocasting approach, the deposited film faithfully reproduces the exterior surface of the resist feature, so an undercut figure would only be used if a non-cylindrical confinement is desired.

In practicing nanocasting, caution is typically employed to removed the metal from above the nanocasting "master" (the resist feature), as the resist feature can in some instances be entirely buried and unavailable for removal. This, however, can be remedied in a number of ways.

Where the deposition technique has a high degree of anisotropy in the deposition (such as metal evaporation), the sidewalls will be very thin near the top of the resist feature, which in some instances can be a cylindrical pillar. This weak point can be subject to direct mechanical disruption allowing the removal of the metal above the resist feature and hence the ZMW location. An isotropic etch, either solution phase or plasma can be used to further thin the film until this weak point separates, achieving the same effect. If the metal deposition step has a low degree of anisotropy (such as sputtering or electroplating), then the resist material can be exposed through chemical mechanical polishing, or ion milling.

Simultaneous with or subsequent to the removal of the metal cap over the resist feature, the resist material is then removed by solvent dissolution, or reactive ion etching. This completes the fabrication steps, provided the appropriate pattern is applied and the other parameters are correctly chosen.

Uses of the Subject Optical Confinements and other Devices

The subject devices including optical confinements and associated optical systems provide a effective means for analyzing molecules and monitoring chemical reactions in real time. The subject device and detection/monitoring methods may be used in a wide variety of circumstances including analysis of biochemical and biological reactions for diagnostic and research applications. In particularly preferred aspects, the present invention is applied in the elucidation of nucleic acid sequences for research applications, and particularly in sequencing individual human genomes as part of preventive medicine, rapid hypothesis testing for genotype-phenotype associations, in vitro and in situ gene-expression profiling at all stages in the development of a multi-cellular organism, determining comprehensive mutation sets for individual clones and profiling in various diseases or disease stages. Other applications include measuring enzyme kinetics, and identifying specific interactions between target molecules and candidate modulators of the target molecule. Further applications involve profiling cell receptor diversity, identifying known and new pathogens, exploring diversity towards agricultural, environmental and therapeutic goals.

In certain embodiments, the subject devices and methods allow high-throughput single-molecule analysis. Single-molecule analysis provides several compelling advantages over conventional approaches to studying biological events. First, the analysis provides information on individual molecules whose properties are hidden in the statistically averaged information that is recorded by ordinary ensemble measurement techniques. In addition, because the analysis can be multiplexed, it is conducive to high-throughput implementation, requires smaller amounts of reagent(s), and takes advantage of the high bandwidth of optical systems such as modern avalanche photodiodes for extremely rapid data collection. Moreover, because single-molecule counting automatically generates a degree of immunity to illumination and light collection fluctuations, single-molecule analysis can provide greater accuracy in measuring quantities of material than bulk fluorescence or light-scattering techniques. As such, single-molecule analysis greatly improves the efficiency and accuracy in genotyping, gene expression profiling, DNA sequencing, nucleotide polymorphism detection, pathogen detection, protein expression profiling, and drug screening.

Single-Molecule Sequencing:

The subject devices, including various forms of optical confinements and the associated optical systems, are particularly suited for multiplexed single-molecule sequencing. Accordingly, the present invention provides a method of simultaneously sequencing a plurality of target nucleic acids. The method generally involves (a) providing an array of optical confinements of the present invention; (b) mixing in the confinements a plurality of target nucleic acid molecules, primers complementary to the target nucleic acid molecules, polymerization enzymes, and more than one type of nucleotides or nucleotide analogs to be incorporated into a plurality of nascent nucleotide strands each being complimentary to a respective target nucleus and molecules; (c) subjecting the mixture to a polymerization reaction under conditions suitable for formation of the nascent nucleotide strands by template-directed polymerization; (d) illuminating the waveguides with an incident light beam; and (e) identifying the nucleotides or the nucleotide analogs incorporated into each nascent nucleotide strand.

The subject sequencing methods can be used to determine the nucleic acid of any nucleic acid molecule, including double-stranded or single-stranded, linear or circular nucleic acids (e.g., circular DNA), single stranded DNA hairpins, DNA/RNA hybrids, RNA with a recognition site for binding of the polymerase, or RNA hairpins. The methods of the present invention are suitable for sequencing complex nucleic acid structures, such as 5' or 3' non-translation sequences, tandem repeats, exons or introns, chromosomal segments, whole chromosomes or genomes.

In one aspect, the temporal order of base additions during the polymerization reaction is identified on a single molecule of nucleic acid. Such identifying step takes place while the template-directed extension of primer or polymerization is taking place within the optical confinement. In a preferred embodiment, single-molecule sequencing is performed in a homogenous assay that does not require transfer, separation, or washing away any reactant or by-product (e.g. fluorophore cleaved from a nucleotide) after each base addition event. In certain aspects of the homogenous assay, single-molecule sequencing is performed without adding reactants to the mixture prior to reading the next base sequence. In this assay, stepwise addition of nucleotides or removal of by-products after each base addition event is not necessary, as diffusion of reactants from a large volume of reagents above the confinement will not interfere with the detection of incorporation. Sequence information is generated continuously as the polymerase continually incorporates the appropriate nucleotides or nucleotide analogs into the nascent DNA strand. For a detailed discussion of such single molecule sequencing, see, e.g., Published U.S. Patent Application No. 2003/0044781, which is incorporated herein by reference in its entirety for all purposes and M. J. Levene, J. Korlach, S. W. Turner, M. Foquet, H. G. Craighead, W. W. Webb, SCIENCE 299:682-686, January 2003 Zero-Mode Waveguides for Single-Molecule Analysis at High Concentrations. There is no loss of synchronization because single molecules are observed separately. This method also allows the use of target nucleic acid molecules taken directly from a biological sample, minimizing the need for cloning, sub-cloning, or amplification of the target nucleic acids before sequencing can take place.

In a preferred embodiment, a polymerase enzyme is provided anchored within the effective observation volume within an optical confinement. Template dependent synthesis of a complementary strand is then carried out while observing the volume, and using labeled nucleotide analogs that are capable of being sequentially incorporated into the growing strand without interruption, e.g., for deprotection, etc. In preferred aspects, nucleotide analogs bearing a label on a non-incorporated phosphate group or derivative, e.g., the beta, gamma, delta, etc. phosphate of a nucleotide polyphosphate which is cleaved from the analog during incorporation, are used in such methods. Such nucleotide analogs provide an advantage of being sequentially incorporated into the growing nucleic acid strand, and having their labeling groups removed in the incorporation process so as to not provide increasing signal noise during synthesis that would result if such labels remained associated with the synthesized strand. In addition, because the incorporation event provides for prolonged presence of the labeled analogs within the observation volume (as compared to random diffusion of non-incorporated analogs into the observation volume), the signal associated within incorporation is readily identifiable. In particularly preferred aspects, for single molecule nucleic acid sequencing applications, a template nucleic acid is used that provides for the redundant or iterative reading/synthesis of tandem repeats of a particular sequence segment of interest. In particular, the systems of the invention typically provide for redundancy in numerous ways, to correct for any errors that may arise in template dependant synthesis by the polymerase enzyme. For example, because the methods of the invention focus on single molecules, redundant processes are employed to assure that mis-incorporation events by a polymerase are corrected for in data analysis.

In a first aspect, such redundancy is supplied by utilizing arrays of multiple different confinements that are being applied to a given sequence of interest, e.g., in a single well of a multi-well plate. In addition to this redundancy, the invention also provides for the iterative sequencing of a given sequence segment (or a copy thereof) multiple times within a single confinement. In a first preferred aspect, such iterative sequencing may be accomplished by providing the sequence segment of interest in a circular template format, so that the polymerase processes around the circular template (allowing the elucidation of the sequence of such template) multiple times. Methods of circularization of nucleic acid segments are known to those of ordinary skill in the art, and are readily applied to template sequences in accordance with the invention.

In another aspect, a similar result is accomplished by using a template-dependant circular template bearing the sequence segment of interest. In particular, such synthesis product will typically include, in a single linear strand, multiple copies of the circular template, again, providing for iterative sequencing of the sequence segment of interest. Further, redundancy is additionally accomplished by circularizing this linear, multi-copy template and iteratively sequencing multiple copies, multiple times.

In another aspect, a similar result is obtained by performing concatmerization of amplicons generated in a single-molecule amplification strategy, several of which are known to those skilled in the art. These strategies can employ dilution to the single molecule level, or isolation of molecules in small micelles in a two-phase emulsion during amplification. The concatmerized strand is then sequenced as a single template, and redundant information is generated from a single molecule in this fashion.

In yet another aspect, a similar result is obtained by using a long double stranded template with nicks and/or gaps at multiple locations along it. The molecule can then be caused to initiate single molecule sequencing at several locations along the strand, each location comprising a confinement that independently sequences the strand. Because the several confinements are acting on the same strand, the result is that the same template is sequenced several times providing redundant information from a single molecule.

Exemplary Experimental Setup:

In practicing a sequencing method of the present invention, a reaction mixture comprising the target nucleic acid(s) of interest, primers complementary to the target nucleic acids, polymerization enzymes, and more than one type of nucleotides or nucleotide analogs, is applied to an array of optical confinements. Preferably, each optical confinement receives only one target nucleic acid molecule that is to be sequenced. This can be achieved by diluting a minute amount of target nucleic acids in a large volume of solution containing the rest of the reactants required for the sequencing process. Alternatively, a non-cylindrical waveguide whose the opening is narrower in lateral dimension than the base, can be used to restrict the entry of multiple target nucleic acids.

Immobilization of the Target Nucleic Acid or the Polymerase to an Optical Confinement:

The target nucleic acid can be immobilized to the inner surface of the optical confinement by a number of ways. For example, the target nucleic acid can be immobilized onto an optical confinement by attaching (1) a primer or (2) a single-stranded target nucleic acid or (3) double-stranded or partially double-stranded target nucleic acid molecule. Thereafter, either (1) the target nucleic acid molecule is hybridized to the attached oligonucleotide primer, (2) an oligonucleotide primer is hybridized to the immobilized target nucleic acid molecule to form a primed target nucleic acid molecule complex, or (3) a recognition site for the polymerase is created on the double-stranded or partially double-stranded target nucleic acid (e.g., through interaction with accessory proteins, such as a primase). A nucleic acid polymerizing enzyme on the primed target nucleic acid molecule complex is provided in a position suitable to move along the target nucleic acid molecule and extend the oligonucleotide primer at the site of polymerization.

In preferred aspects, as described previously, the polymerization enzyme is first attached to a surface of the subject optical confinement within the effective observation volume of the confinement, and in a position suitable for the target nucleic acid molecule complex to move relative to the polymerization enzyme.

One skilled in the art will appreciate that there are many ways of immobilizing nucleic acids and enzymes onto an optical confinement, whether covalently or noncovalently, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. Antibodies that specifically bind to the target nucleic acids or polymerases can also be employed as the binding moieties. In addition, a silyl moiety can be attached to a nucleic acid directly to a substrate such as glass using methods known in the art.

Where desired, the polymerases may be modified to contain one or more epitopes such as Myc, HA (derived from influenza virus hemagglutinin), poly-histadines, and/or FLAG, for which specific antibodies are available commercially. In addition, the polymerases can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin are available, and can be used to coat the surface of an optical confinement of the present invention.

The binding moieties or agents of either the polymerases or nucleic acids they immobilize can be applied to the support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

Reaction Mixture: Labeled Nucleotides, Polymerases, and Primers:

The various types of nucleotides utilized in accordance with the single-molecule sequencing method are conjugated with detectable labels so that a photon detector can detect and distinguish their presence within the subject optical confinements. Preferred labels are luminescent labels, and especially fluorescent or chromogenic labels.

A variety of functional groups used as detectable labels in nucleotides has been developed in the art. Table 1 lists numerous examples of such functional groups. Additional examples are described in U.S. Pat. No. 6,399,335, published U.S. Patent Application No. 2003/0124576, and The Handbook—'A Guide to Fluorescent Probes and Labeling Technologies, Tenth Edition' (2005) (available from Invitrogen, Inc.,/Molecular Probes), all of which are incorporated herein by reference.

TABLE 1

Exemplary detectable label functional groups

| | |
|---|---|
| 4-aminophenol | 6-aminonaphthol |
| 4-nitrophenol | 6-nitronaphthol |
| 4-methylphenol | 6-chloronaphthol |
| 4-methoxyphenol | 6-bromonaphthol |
| 4-chlorophenol | 6-iodonaphthol |
| 4-bromophenol | 4,4'-dihydroxybiphenyl |
| 4-iodophenol | 8-hydroxyquinoline |
| 4-nitronaphthol | 3-hydroxypyridine |
| 4-aminonaphthol | umbelliferone |
| 4-methylnaphthol | Resorufin |
| 4-methoxynaphthol | 8-hydroxypyrene |
| 4-chloronaphthol | 9-hydroxyanthracene |
| 4-bromonaphthol | 6-nitro9-hydroxyanthracene |
| 4-iodonaphthol | 3-hydroxyflavone |
| 6-methylnaphthol | fluorescein |
| 6-methoxynaphthol | 3-hydroxybenzoflavone |

Using these or other suitable functional groups known in the art, a vast diversity of fluorophores suitable for the present sequencing method can been generated. They include but are not limited to 4-acetamido-4'-isothiocyanatostilbene-2,2'disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonc acid; 4,4'-diisothiocyanatostilbene-2,2'-disulfonic acid; 5-[dimethylamino]naphthalene-1-sulfonyl chloride (DNS, dansyl chloride); 4-(4'-dimethylaninophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamnine B, sulforhodamine 101 and sulfonyl chloride derivative of sulforhodamnine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Additional fluorophores applicable for the subject sequencing methods are disclosed in U.S. Pat. No. 5,866,366 and WO 01/16375, both of which are incorporated herein by reference.

The labels can be attached to the phosphate backbone, on the base, on the ribose unit, or a combination thereof. Preferred labels are those that do not substantially impede the continuous addition of nucleotides in a sequencing reaction. Such labels include those linked to the alpha phosphate, the beta phosphate, the terminal phosphate, or the delta or more distal phosphates in tetra, penta or hexa phosphate nucleotides, or the base unit of a nucleotide.

Nucleotides comprising labeled terminal phosphates (e.g., the gamma phosphate as in dNTP), are particularly preferred because no additional means is required to remove the label in the sequencing procedure. During the process of nucleic acid polymerization, the bond cleavage in the nucleotide occurs between the alpha and the beta phosphate, causing the beta and terminal phosphate (e.g., the gamma phosphate as in dNTP) to be released from the site of polymerization. As such, the label attached to the terminal phosphate is separated from the nascent strand once the nucleotide is being incorporated. In general, terminal-phosphate-linked nucleotides may comprise three or more phosphates, typically about three to about six phosphates, preferably about three to about five phosphates. Table 1 lists numerous examples of nucleotides with labeled terminal phosphates. Many other terminal-phosphate-linked nucleotides have been developed and are detailed in U.S. patent application No. 2003/0124576, which is incorporated herein by reference in its entirety.

TABLE 2

Adenosine-5'-(γ-4-nitrophenyl)triphosphate
Guanosine-5'-(γ-4-nitrophenyl)triphosphate
Cytosine-5'-(γ-4-nitrophenyl)triphosphate
Thymidine-5'-(γ-4-nitrophenyl)triphosphate

TABLE 2-continued

Uracil-5'-(γ-4-nitrophenyl)triphosphate
3'-azido-3'-deoxythymidine-5'-(γ-4-nitrophenyl)triphosphate
3'-azido-2',3'-dideoxythymidine-5'-(γ-4-nitrophenyl)triphosphate
2',3'-didehydro-2',3'-dideoxythymidine-5'-(γ-4-nitrophenyl)triphosphate
Adenosine-5'-(γ-4-aminophenyl)triphosphate
Adenosine-5'-(γ-4-methylphenyl)triphosphate
Adenosine-5'-(γ-4-methoxyphenyl)triphosphate
Adenosine-5'-(γ-4-chlorophenyl)triphosphate
Adenosine-5'-(γ-4-bromophenyl)triphosphate
Adenosine-5'-(γ-4-iodophenyl)triphosphate
Adenosine-5'-(γ-4-nitronaphthyl)triphosphate
Adenosine-5'-(γ-4-aminonaphthyl)triphosphate
Adenosine-5'-(γ-4-methylnaphthyl)triphosphate
Adenosine-5'-(γ-4-methoxynaphthyl)triphosphate
Adenosine-5'-(γ-4-chloronaphthyl)triphosphate
Adenosine-5'-(γ-4-bromonaphthyl)triphosphate
Adenosine-5'-(γ-4-iodonaphthyl)triphosphate
Adenosine-5'-(γ-6-methylnaphthyl)triphosphate
Adenosine-5'-(γ-6-methoxynaphthyl)triphosphate
Adenosine-5'-(γ-6-aminonaphthyl)triphosphate
Adenosine-5'-(γ-6-nitronaphthyl triphosphate
Adenosine-5'-(γ-6-chloronaphthyl)triphosphate
Adenosine-5'-(γ-6-bromonaphthyl)triphosphate
Adenosine-5'-(γ-6-iodonaphthyl)triphosphate
Adenosine-5'-(γ-4'-hydroxybiphenyl)triphosphate
Adenosine-5'-(γ-8-quinolyl)triphosphate
Adenosine-5'-(γ-3-pyridyl)triphosphate
Adenosine-5'-(γ-umbelliferone)triphosphate
Adenosine-5'-(γ-resorufin)triphosphate
Adenosine-5'-(γ-pyrene)triphosphate
Adenosine-5'-(γ-anthracene)triphosphate
Adenosine-5'-(γ-6-nitroanthracene)triphosphate
Adenosine-5'-(γ-flavonyl)triphosphate
Adenosine-5'-(γ-fluorescein)triphosphate
Adenosine-5'-(γ-benzoflavone)triphosphate
Adenosine-5'-(γ-(4-nitrophenyl)-γ'-(4-aminophenyl)triphosphate
Adenosine-5'-(γ-(4-nitrophenyl)-γ'-(4-nitronaphthyl)triphosphate Nucleotides comprising modified phosphate backbones can also be used. For example, the modified component can be a phosphordiamidate, methylphosphonate, alkyl phosphotriester, formacetal, phosphorodithioate, phosphothioate, phosphoramidothioate, phosphoramidate, or an analog thereof In some embodiments, the nucleotides or nucleotide analogs used in the present invention are reversible extension terminators comprising reversible blocking groups. In some embodiments, the blocking group on a reversible extension terminator is linked to a detectable label. In other embodiments, the blocking group and the detectable label are located on different positions of a nucleotide. In yet other embodiments, the blocking group is also a label.

An illustrative reversible extension terminator comprises a labeled ribose unit at the 3' end. Each label on the ribose unit, typically acts as a reversible blocking group that must be removed before the next nucleotide addition event can take place during a polymerization reaction. Preferred 3'-ribose labels comprise photo-removable functional groups that can be deprotected upon exposure to a light beam at a suitable wavelength.

Figure 14:
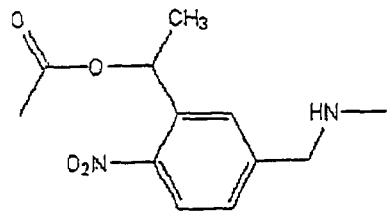
FIG. 14 depicts several exemplary photocleavable blockers and the applicable wavelength applied to cleave the blocking groups.
Figure 14:
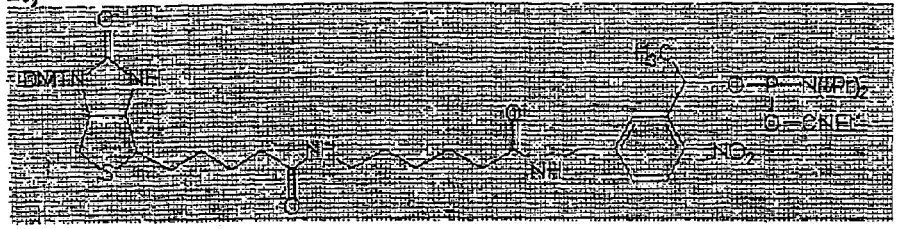
Figure 14:
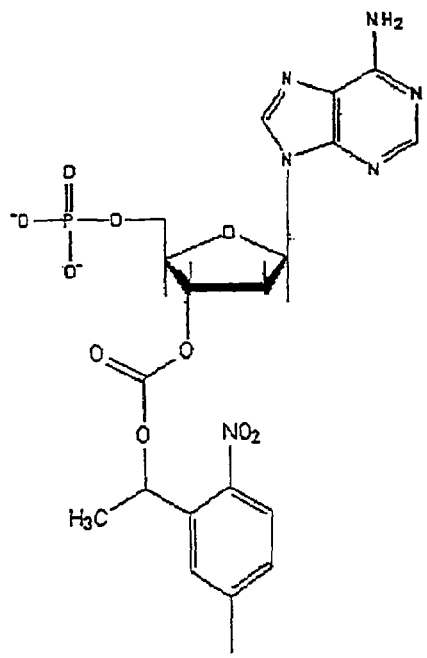
Figure 14:
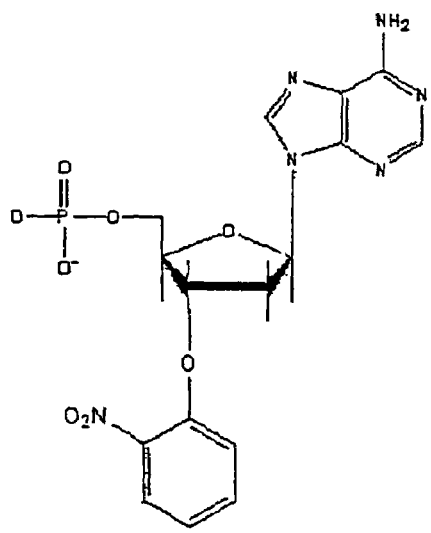
Figure 15:
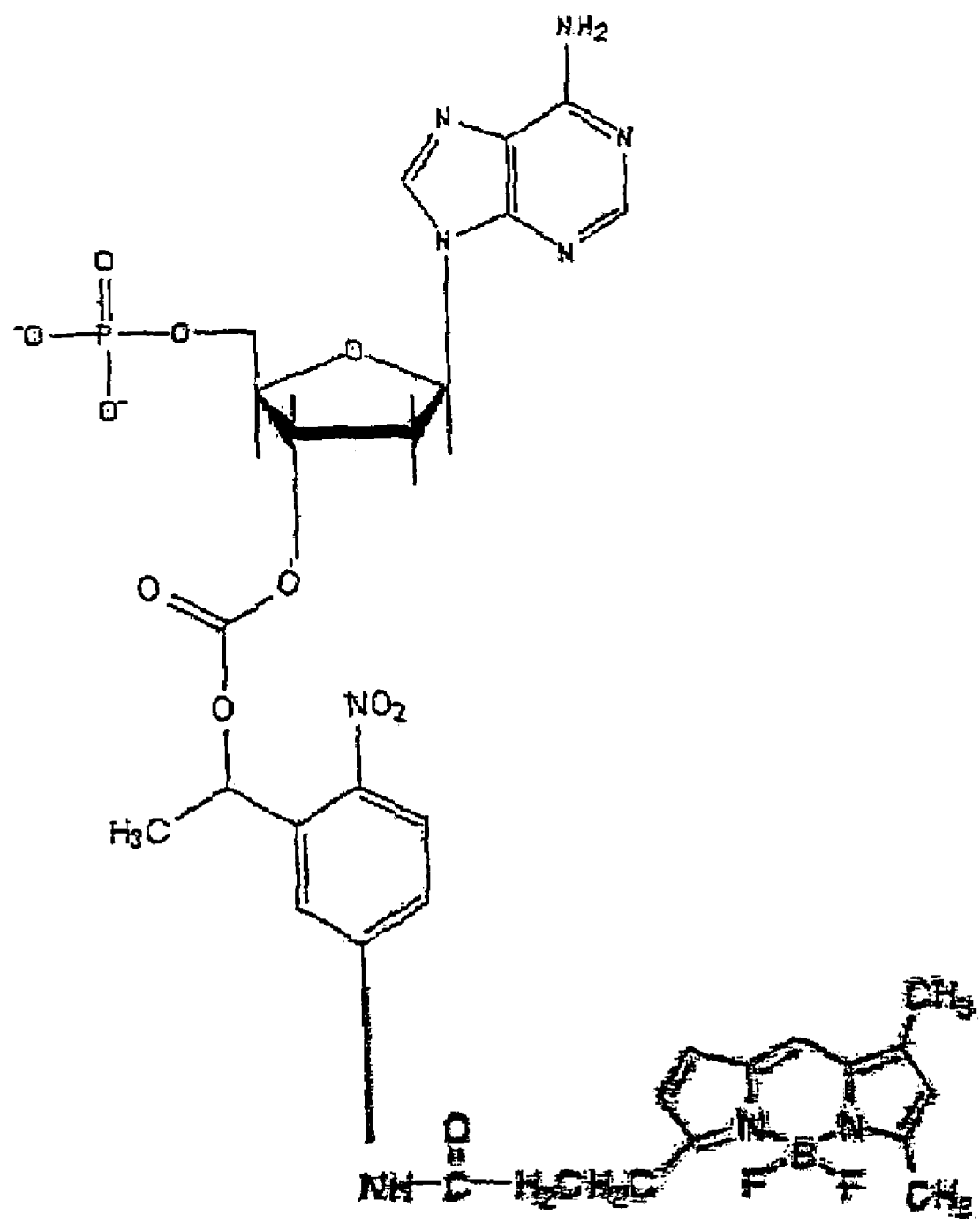
FIG. 15 depicts an exemplary reversible extension terminator in which the photocleavable blocker is conjugated to a detectable label (e.g., fluorescent label).

In another example, the reversible blocking group is located at the 2' or the 4' position of the ribose unit of nucleotide. In yet another embodiment, the reversible blocking group is linked to or conjugated to the base (adenine, thymine, cytosine, guanine, or uracil) a nucleotide. Non-limiting examples of reversible blocking groups, and especially photocleavable blocking groups include but are not limited to those molecules depicted in FIGS. 14 and 15 and those described in the co-pending application Ser. No. 60/649,009, which is incorporated herein by reference in its entirety.

The wavelength used to cleave the photocleavable blocking groups will depend on the choice of the locking group. The wavelength may range from about 320 nm to about 800 nm. In some embodiment, the wavelength for cleaving the blocking group is about the same as the wavelength used to detect the label. In other embodiments, the wavelength for cleaving the blocking group is different from the wavelength used to detect the label.

In some embodiments, it is advantageous to use a mixture of labeled nucleotides that is substantially free of unlabeled nucleotides. Such composition and the uses thereof for sequencing are detailed in co-pending application Ser. No. 60/651,846, which is incorporated herein. Briefly, the composition is prepared by treating a mixture comprising labeled and unlabeled nucleotides or nucleotide analogs with an agent that specifically modifies unlabeled or incorrectly labeled nucleotides or nucleotide analogs to reduce their ability to be used in a hybridization or sequencing assay. Preferably, the agent used specifically modifies unlabeled or incorrectly labeled nucleotides analogs to render them incapable of being used in a hybridization or sequencing assay. For example, the nucleotides can be modified so that they no longer contain structures generally needed for the Watson Crick base pairing in a hybridization or template-directed sequencing assay. In some embodiments, for example, base units of the nucleotides are modified. In some embodiments, phosphate groups, preferably terminal phosphate groups, of the nucleotides or nucleotide analogs are modified to yield molecules that are incorporated to a lesser extent into a nascent nucleic acid strand during a template-directed polymerization reaction. In more preferred embodiments, the terminal phosphate groups of a nucleotide or nucleotide analogs are modified to yield molecules that cannot or that substantially cannot be incorporated into a nascent nucleic acid strand during a template-directed polymerization reaction.

The agents can comprise one or more enzymes. A variety of enzymes known in the art are suitable for modifying the nucleotides or nucleotide analogs, e.g. by cleaving or altering the configuration of the sugar, base, or phosphates, so as to disrupt the specific Watson Crick base pairing. Exemplary agents include but are not limited to guanine or adenine P-ribosyl transferase, purine nucleoside phosphorylase, AMP nuleosidase, nucleoside deoxyribosyl transferase for purines, and orotate P-ribosyl transferase, thymidine phosphorylase, thymidine or uridine nucleosidase, uridine phosphorylase, pyrimidine nucleoside phosphorylase nucleoside deoxyribosyl transferase.

Enzymes applicable for modifying the terminal phosphate groups of nucleotides or nucleotide analogs include a wide array of phosphatases. An example of such enzyme is Shrimp Alkaline Phosphatase (SAP) that can remove the gamma and beta phosphates from a deoxynucleoside triphosphate (dNTP). The enzyme can convert specifically unlabeled dNTP into a nucleoside monophosphate dNMP which is generally incapable of being utilized by a polymerase enzyme in a template-directed sequencing reaction. It has been shown, that this phosphatase selectively modify nucleotides that are not labeled, e.g. at the terminal phosphate. Therefore, in a mixture of terminal phosphate-labeled and unlabeled nucleotides, the SAP will preferentially act on unlabeled nucleotides, leaving a larger proportion of labeled nucleotides available for incorporation in a sequencing reaction.

Other suitable phosphatases that can be used include but are not limited to calf intestinal alkaline phosphatases, and/or phosphatases of other mammals, crustaceans, and other animals. Examples of phosphatases that may be useful practicing the present invention can be found in US 20040203097, US 20040157306, US 0040132155; and US 20040110180.

Any other naturally occurring or synthetic phosphatases or phosphatases made by recombinant DNA technology can also be used so long as they specifically or preferentially convert unlabeled nucleotides or analogs (as compared to labeled nucleotides), to molecules that are substantially incapable of being utilized by a polymerization enzyme. Directed molecular evolution can also be used to enhance and extend the activity of related enzymes to yield the desired property described above. A wide variety of mutagenesis techniques, both in silicon and in situ, are available in the art. An example of a mutagenesis or screening assay for generating such enzymes can involve a first test for abrogation of polymerization in the system with unlabeled nucleotides, and a second screen checking for the retention of polymerization activity in the presence of labeled nucleotides. Both of these screens can be performed in the context of a highly multiplexed parallel assay. Enzymes showing some beneficial specificity can be retained, mutated by some method, and then re-screened. Methods such as these have been shown to produce many orders of magnitude improvement in specificity and performance.

Enzymes capable of selectively or preferentially modifying a subset of unlabeled nucleotides can also be employed. For example, creatine kinase enzyme is specific for the removal of a phosphate from adenoside triphosphate, and will not act on other bases. Other enzymes that selectively or preferentially act on one or more types of unlabeled nucleotides can also be used.

The nucleotide modifying enzymes described above can be used to pre-treat the nucleotides or nucleotide analogs, or can be used in the hybridization and/or sequencing reaction mixture, e.g., along with other hybridization or sequencing reagents.

The reaction conditions under which the modification of the nucleotides takes place will vary depending on the choice of the modifying enzymes. In one aspect, the conditions may be set within the following parameters: pH is between 4.0 and 12.0, more preferably between pH 6.0 and 10.0, more preferably between 7.0 and 9.0, more preferably less than 8, more preferably between 7 and 8, and most preferably pH 7.5 and 8.5, preferably controlled by a buffer. The buffer can be Tris-based preferably at pH 7.5 to pH 8.5. Other buffers may be used such as, but not limited to: organic buffers such as MOPS, HEPES, TRICINE, etc., or inorganic buffers such as phosphate or acetate. Buffers or other agents may be added to control the pH of the solution thereby increasing the stability of the enzymes. Where desired, reducing agent such as but not limited to dithiothreitol (DTT) or 2-mercaptoethanol may be added to limit enzyme oxidation that might adversely affect stability of the enzymes. The choice of specific reaction conditions including various buffers and pH conditions is within the skill of practitioners in the field, and hence is not further detailed herein.

Upon completion of the pre-treatment, the enzymes can be heat-inactivated by raising the reaction temperature to at least about 65° C., preferably between about 65° C. to about 80° C. Alternatively, the enzymes can be depleted from the reaction mixture by, e.g., centrifugation through a filter (e.g., Millipore) that has a molecular weight cutoff smaller than the size of the enzyme.

After the treatment, the mixture generally comprises less than about 30%, preferably less than about 20%, more preferably less than about 10%, more preferably less than about 5%, more preferably less than about 1%, more preferably less than about 0.5%, or more preferably less than about 0.1%, and even more preferably less than 0.01% of unlabeled nucleotides or unlabeled nucleotide analogs. This enriched mixture of labeled nucleotides or nucleotide analogs is particularly useful for high-resolution detection of the labeled nucleotides in a single-molecule sequence reaction.

Importantly, the result of the foregoing treatment is a process for synthesis of nucleic acids, preferably for elucidating a template sequence using substantially only nucleotides, e.g., substantially complete replacement of native nucleotides with nucleotide analogs, and particularly labeled analogs. Such template dependant synthesis in the presence of substantially only nucleotide analogs, and particularly labeled analogs, also referred to as substantially complete replacement, in sequencing operations is considerably different from previously described sequencing methods where a single nucleotide is substituted with a labeled chain terminating nucleotide among the remaining three natural nucleotides, or where a polymerase template complex are interrogated with only one analog at a time to determine whether such analog is incorporated.

Another type of suitable nucleotides for the subject sequencing methods allows detection via fluorescence resonance energy transfer (FRET). In FRET, an excited fluorophore (the donor) transfers its excited state energy to a light absorbing molecule (the acceptor) in a distance-dependent manner. The limitation on the distance over which the energy can travel allows one to discern the interactions between labeled molecules and entities in close proximity. Nucleotides of this type can comprise a donor fluorophore attached to the base, ribose or preferably the phosphate backbone (e.g., attached to the terminal phosphate), and an acceptor fluorophore attached to the base, ribose or the phosphate backbone where the donor is not attached. In a preferred embodiment, the donor fluorophore is attached to the terminal phosphate, and an acceptor fluorophore is linked to the base or the ribose unit of the nucleotide. Upon incorporation of this type of nucleotide into the nascent strand, a fluorescent signal can be detected which can be caused by the release of poly-phosphate that is no longer quenched. By determining the order of the fluorescent poly-phosphate that is released upon incorporating a complementary nucleotide during the polymerization event, one can deduce the base sequence of the target nucleic acid. Additional examples of this type of nucleotides is disclosed in U.S. application No. 20030194740, which is incorporated herein by reference.

In another embodiment, the donor fluorophore can be present in a nucleotide, and the acceptor is located in the polymerase, or vice versa. Where desired, the fluorophore in the polymerase can be provided by a green fluorescent protein (GFP) or a mutant thereof that has a different emission and/or absorption spectrum relative to the wildtype green fluorescent protein. For example, the GFP mutant H9-40 (Tsien et al., Ann. Rev. Biochem. 67: 509 (1998)) which is excited at 399 nm and emits at 511 nm, may serve as a donor fluorophore for use with BODIPY, fluorescein, rhodamine green and Oregon green. In addition, tetramethylrhodamine, Lissamine™, Texas Read and napthofluorescein can be used as acceptor fluorophores with this GFP mutant.

Other representative donors and acceptors capable of fluorescence energy transfer include, but are not limited to, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino4-trifluoromethylcouluarin (Coumaran 151); cyanine dyes; cyanosine; 4',6-diaminidino-2-phenylindole (DAPI); 5', 5"-dibromopyrogallol-sulfonaphthalein (Bromopyrogallol Red); 7-diethylamino-3-(4'-isothiocyanatophenyl)4-methylcoumarin;
diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy 4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.™. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

In alternative configurations, both donor and acceptor fluorophores may be present upon each nucleotide analog, where the donor provides a substantially uniform excitation spectrum, but donates energy to an acceptor that provides an emission spectrum that is different for each type of analog, e.g., A, T, G, or C. Such configurations provide an ability to utilize a single excitation source for multiple different emission profiles, reducing energy input requirements for the systems utilized.

In addition, xanthene dyes, including fluoresceins and rhodamine dyes can be used as donor and acceptor pairs. Many of these dyes contain modified substituents on their phenyl moieties which can be used as the site for bonding to the terminal phosphate or the base of a nucleotide. Where desired, acceptors acting as quenchers capable of quenching a wide range of wavelengths of fluorescence can be used. Representative examples of such quenchers include 4-(4'-dimethylaminophenylaz-o)-benzoic acid (DABCYL), dinitrophenyl (DNP) and trinitrophenyl (TNP).

The polymerization enzymes suitable for the present invention can be any nucleic acid polymerases that are capable of catalyzing template-directed polymerization with reasonable synthesis fidelity. The polymerases can be DNA polymerases or RNA polymerases, a thermostable polymerase or a thermally degradable polymerase wildtype or modified. Non-limiting examples for suitable thermostable polymerases include polymerases from *Thermus aquaticus, Thermus caldophilus, Thermus filiformis, Bacillus caldotenax, Bacillus stearothermophus, Thermus thermophilus, Pyrococcus woesei, Pyrococcus furiosus, Thermococcus litoralis*, and *Thermotoga maritima*. Useful thermodegradable polymersases include *E. coli* DNA polymerase, the Klenow fragment of *E. coli* DNA polymerase, T4 DNA polymerase, T7 DNA polymerase.

Additional examples of polymerization enzymes that can be used to determine the sequence of nucleic acid molecules include *E. coli* T7, T3, SP6 RNA polymerases and AMV, M-MLV and HIV reverse transcriptases. The polymerase can be bound to the primed target nucleic acid sequence at a primed single-stranded nucleic acid, an origin of replication, a nick or gap in a double-stranded nucleic acid, a secondary structure in a single-stranded nucleic acid, a binding site created by an accessory protein, or a primed single-stranded nucleic acid.

In one preferred embodiment, the polymerization enzymes exhibit enhanced efficiency as compared to the wildtype enzymes for incorporating unconventional or modified nucleotides, e.g., nucleotides linked with fluorophores. Recombinant DNA techniques can be used to modify the wildtype enzymes. Such techniques typically involve the construction of an expression vector or a library of expression vector, a culture of transformed host cells under such condition such that expression will occur. Selection of the polymerases that are capable of incorporating unconventional or modified nucleotides can be carried out using any conventional sequencing methods as well as the sequencing methods disclosed herein.

In another preferred embodiment, sequencing is carried out with polymerases exhibiting a high degree of processivity, i.e., the ability to synthesize long stretches of nucleic acid by maintaining a stable nucleic acid/enzyme complex. A processive polymerase can typically synthesize a nascent strand over about 10 kilo bases. With the aid of accessory enzymes (e.g., helicases/primases), some processive polymerases can synthesize even over 50 kilobases. For instance, it has been shown that T7 DNA polymerase complexed with helicase/primase can synthesize several 100 kilobases of nucleotides while maintaining a stable complex with the target nucleic acid (Kelman et al., "Processivity of DNA Polymerases: Two Mechanisms, One Goal" Structure 6: 121-125 (1998)).

In another preferred embodiment, sequencing is performed with polymerases capable of rolling circle replication, i.e., capable of replicating circular DNA templates including but not limited to plasmids and bacteriophage DNA. A preferred rolling circle polymerase exhibits strand-displacement activity, and preferably has reduced or essentially no 5' to 3' exonuclease activity. Strand displacement results in the synthesis of tandem copies of a circular DNA template, thus allowing re-sequencing the same DNA template more than once. Re-sequencing the same DNA template greatly enhances the chances to detect any errors made by the polymerase, because the same errors unlikely would be repeated by the polymerase and the same error certainly would not be exponentially amplified as in a polymerase chain reaction.

Non-limiting examples of rolling circle polymerases suitable for the present invention include but are not limited to T5 DNA polymerase (Chatterjee et al., Gene 97:13-19

(1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1DNA polymerase (Jung et al., Proc. Natl. Aced. Sci. USA 84:8287 (1987), and Zhu and Ito, Biochim. Biophys. Acta. 1219:267-276 (1994)), Klenow fragment of DNA polymerase I (Jacobsen et al., Eur. J. Biochem. 45:623-627 (1974)).

A preferred class of rolling circle polymerases utilizes protein priming as a way of initiating replication. Exemplary polymerases of this class are modified and unmodified DNA polymerase, chosen or derived from the phages (Φ29, PRD1, Cp-1, Cp-5, Cp-7, Φ15, Φ1, Φ21, Φ25, BS 32 L17, PZE, PZA, Nf, M2Y (or M2), PR4, PR5, R722, B103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5'end. To initiate replication, a histone-like viral protein forms a nucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (TP-dAMP) slides back one position in the DNA to recover the terminal nucleotide After initiation, the same DNA polymerase replicates one of the DNA strands while displacing the other. The high processivity and strand displacement ability of Φ29 DNA polymerase makes it possible to complete replication of the Φ29TP-containing genome (TP-DNA) in the absence of any helicase or accessory processivity factors (reviewed by Serrano et al., The EMBO Journal 16(9): 2519-2527 (1997)).

Modified 429 DNA polymerases having reduced 5' to 3' exonuclease activity have also been described (U.S. Pat. Nos. 5,198,543 and 5,001,050, both being incorporated herein). These polymerases are particularly desirable for sequencing as the 5' to 3' exonucleases, if present excessively, may degrade the nascent strand being synthesized.

Strand displacement can be enhanced through the use of a variety of accessory proteins. They include but are not limited to helicases (Siegel et al., J. BioL Chem. 267:13629-13635 (1992)), herpes simplex viral protein ICP8 (Skaliter and Lehman, Proc. Natl, Acad. Sci. USA 91(22):10665-10669 (1994)), single-stranded DNA bindi proteins (Rigler and Romano, J. Biol. Chem. 270: 8910-8919 (1995)), adenovirus DNA-binding protein (Zijderveld and van der Vliet, J. Virology 68(2): 1158-1164 (1994)), and BMRF1 polymerase accessory subunit (Tsurumi et J. Virology 67(12): 7648-7653 (1993)).

In a preferred embodiment, the sequence reaction involves a single complex of strand-displacement polymerization enzyme and a circular target DNA, which is immobilized to an optical confinement. Upon mixing the labeled nucleotides or nucleotide analogs and the primers, the strand-displacement polymerization enzyme directs the synthesis of a nascent strand and a time sequence of incorporating the various types of labeled nucleotides or nucleotide analogs into the nascent strand is registered. Where desired, the strand-displacement polymerase is allowed to synthesize multiple tandem repeats of the target DNA, and thus effecting re-sequencing the same circular DNA target multiple times. It is preferably to register the time sequence of the nucleotides or nucleotide analogs incorporated into at least two tandem repeats of the target DNA molecule, more preferably at least about three to about ten or about three to about one hundred tandem repeats, and preferably no more than about one million repeats. This multiple rounds of or redundant sequencing can take place under an isothermal condition and/or at ambient temperature.

Using the subject method, sequencing can be carried out at the speed of at least 1 base per second, preferably at least 10 bases per second, more preferably at least 100 bases per second. It has been reported that polymerases can polymerize 1,000 bases per second in vivo and 750 bases per second in vitro (see, e.g. Kelman et al., "Processivity of DNA Polymerases: Two Mechanisms, One Goal," Structure 6: 121-125 (1998); Carter et al., "The Role of Exonuclease and Beta Protein of Phage Lambda in Genetic Recombination. II. Substrate Specificity and the Mode of Action of Lambda Exonuclease," J. Biol. Chem. 246: 2502-2512 (1971); Tabor et al., "*Escherichia coli* Thioredoxin Confers Processivity on the DNA Polymerase Activity of the Gene 5 Protein of Bacteriophage T7, " J. Biol. Chem. 262: 16212-16223 (1987); and Kovall et al., "Toroidal Structure of Lambda-Exonuclease" Science 277: 1824-1827 (1997), which are hereby incorporated by reference).

Reaction Conditions:

The sequencing procedures of the present invention are performed under any conditions such that template-directed polymerization can take place using a polymerization enzyme. In one aspect, the substrates of the polymerization enzyme, namely the various types of nucleotides present in the sequence reaction, are adjusted to a physiologically relevant concentration. For example, the nucleotides used in the sequencing reaction are present at a concentration about Michaelis constant of the polymerization enzyme. Such concentration typically ranges from about 1 micromolar to about 50 micromolar or about 100 micromolar.

The sequencing procedures can also be accomplished using less than four labels employed. With three labels, the sequence can be deduced from sequencing a nucleic acid strand (1) if the fourth base can be detected as a constant dark time delay between the signals of the other labels, or (2) unequivocally by sequencing both nucleic acid strands, because in this case one obtains a positive fluorescence signal from each base pair. Another possible scheme that utilizes two labels is to have one base labeled with one fluorophore and the other three bases with another fluorophore. In this case, the other three bases do not give a sequence, but merely a number of bases that occur between the particular base being identified by the other fluorophore. By cycling this identifying fluorophore through the different bases in different sequencing reactions, the entire sequence can be deduced from sequential sequencing runs. Extending this scheme of utilizing two labels only, it is even possible to obtain the full sequence by employing only two labelled bases per sequencing run.

The sequencing procedures can be performed under an isothermal condition, at ambient temperature, or under thermal cycling condition. The choice of buffers, pH and the like is within the skill of practitioners in the art, and hence is not detailed herein.

Detection:

The subject sequencing method requires the imaging of individual molecules confined in an optical confinement. The polymerase and/or the nucleotides are labeled with fluorophores that emit a distinguishable optical signal when a particular type of nucleotide is incorporated into the nascent strand. The sequence of the distinguishable signals is detected as the nucleotides are sequentially added to the nascent strand within the optical confinement. In a preferred embodiment, such detection is performed without the need to transfer, separation or washing away any reactant or by-product (e.g. fluorophore cleaved from a nucleotide) after each nucleotide addition event. In one aspect of this preferred embodiment, sequence detection is performed without adding reactants to the mixture prior to reading the next base sequence nucleotide to be incorporated.

Imaging individual molecules confined in the subject optical confinements is performed with the aid of an optical system. Such system typically comprises at least two elements, namely an excitation source and a photon detector. Numerous examples of these elements are described above.

In a preferred embodiment, the excitation source is a laser, preferably a polarized laser. The choice of laser light will depend on the fluorophores attached to the different type of nucleotides and/or the polymerases. For most of the flurophorescent compounds, the required excitation light is within the range of about 300 nm to about 700 nm. For proteinaceous fluorophores such as green-fluorescent protein and mutants thereof, the excitation wavelength may range from about 488 nm to about 404 nm. Those skilled in the art will know or will be able to ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference).

Another consideration in selecting an excitation source is the choice between one-photon and multiphoton excitation of fluorescence. Multiphoton excitation coupled with detection, also known as multiphoton micropscopy ("MPM"), provides enhanced sensitivity and spatial resolution. MPM is a form of laser-scanning microscopy that uses localized nonlinear excitation to excite fluorescence within a thin raster-scanned plane. In MPM, as in conventional laser-scanning confocal microscopy, a laser is focused and raster-scanned across the sample. The image consists of a matrix of fluorescence intensity measurements made by digitizing the detector signal as the laser sweeps back and forth across the sample. Two-photon excitation probabilities are extremely small, and focusing increases the local intensity at the focal point: Although two-photon excited fluorescence is usually the primary signal source in MPM, three-photon or more excited fluorescence and second or third-harmonic generation can also be used for imaging. See, e.g., a review of multiphoton micropscopy in Webb et al. *Nature Biotechnology* (2003) 21: (11) 1251-1409. A preferred MPM setup comprises MPM laser scanning microscopes and second-harmonic imaging, equipped with femtosecond mode-locked titanium sapphire lasers operating at wavelengths from about 700 to 1,000 nm. Such setup can capture more than about 100 photons per pixel in most of the conventional imaging multiphoton microscope.

The sequence of the distinguishable signals can also be detected by other optical systems comprising elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope.

A preferred combination comprises wide field CCD or ICCD and intensified video imaging microscopes with digital image processing capability, as well as Fluorescence Photobleaching Recovery (FPR) and Fluorescence Correlation Spectroscopy (FCS) coupled with confocal multiphoton capability and continuous data acquisition and control. Such set up may further comprise modular instrument for quasi-elastic light scattering, laser DIC interferometry, correlation spectroscopy instrumentation, components of optical force microscopy, and Time Correlated Single Photon Counting (TCSPC).

These optical systems may also comprise optical transmission elements such as diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements.

These and other optical components known in the art can be combined and assembled in a variety of ways to effect detection of the distinguishable signals emitted from the sequencing reaction. Preferred devices allow parallel data collection using arrays having a large number of optical confinements, where simultaneous and independent sequencing of nucleic acids takes place. In one aspect, the preferred system can collect and process signals from more than $10^4$ optical confinements, more than $2 \times 10^4$ optical confinements, or more than $10^5$ optical confinements, or more than $2 \times 10^5$ optical confinements, or preferably more than $10^6$, or preferably more than $2 \times 10^6$ optical confinements, and even more preferably more than $10^7$ or $2 \times 10^7$ optical confinements. In another aspect, the preferred setup can monitor in real time the simultaneous-and independent sequencing of nucleic acids at a speed of about 1 base per second, preferably at a speed of about 10 bases per second, more preferably at a speed of about 100 bases per second and even more preferably at 1,000 bases per second. As such, the massive parallelism coupled with the rapid sequencing reaction can provide an overall sequencing output greater than 100,000 bases per second. The overall output can be scaled up to at least 1 megabase per second, preferably 10 or more megabases per second. Further by obtaining such date from multiple different sequence fragments e.g., in from two or more different reaction volumes, one can obtain independent sequences, e.g. from contiguous fragments of genomic DNA, allowing the high rate of throughput that is directly applicable to genomic sequencing.

Other Single-Molecule Applications:

The subject optical confinements and arrays of optical confinements find utility in many other chemical and biological applications where single molecule analyses are desired. In general, the subject optical confinements are applicable for any single molecule analysis involving any reagent that can be attached to the surface and for which substrates can be labeled, including, enzymes, nucleic acids, antibodies, antigens, and the like. Such applications include discerning interactions involving biological molecules such as proteins, glycoproteins, nucleic acids, and lipids, as well as inorganic chemicals, or any combinations thereof. The interactions may be between nucleic acid molecules, between nucleic acid and protein, and between protein and small molecules.

Abnormalities in interactions involving biological molecules have long been acknowledged to account for a vast number of diseases including, numerous forms of cancer, vascular diseases, neuronal, and endocrine diseases. An abnormal interaction, in form of e.g., constitutive activation and premature inactivation of a signaling complex, are now known to lead to aberrant behavior of a disease cell. In the case of cancer, abnormal interactions between two signaling transduction molecules, such as growth factor receptors and their corresponding ligands, may result in dysfunction of cellular processes, which ultimately lead to dysregulated growth, lack of anchorage inhibition, genomic instability and/or propensity for cell metastasis.

A specific interaction between biological or chemical molecules typically involves a target molecule that is being investigated and a probe suspected to be able to specifically interact with the target. In practicing the subject methods, the target and the probe are placed within an optical confinement. The target-probe complex can be a protein-protein complex, a glycoprotein-protein complex (e.g., receptor and ligand complex), a protein-nucleic acid complex (e.g., transcription factor and nucleic acid complex), a protein-lipid complex, and complex of inorganic or organic small molecules.

Preferably, each optical confinement contains only one target that is being investigated. This can be achieved by diluting a minute amount of target in a large volume of solution, such that deposition over an array of confinements results in a primary distribution, or a majority of confinements will have a single target molecule disposed there. Alternatively, a non-cylindrical waveguide, wherein the opening of the waveguide core is narrower in lateral dimension than the base, can be used to restrict the entry of multiple target proteins while permitting the entry of a number of smaller probes.

The target or probe can be immobilized onto the inner surface of the optical confinement by any of the methods applicable for immobilizing and depositing the polymerases described in the section above. Such methods encompass the uses of covalent and noncovalent attachments effected by a variety of binding moieties. The choice of the binding moieties will depend on the nature of the target and/or the probe. For example, the binding moieties can be synthetically linked to the protein target or the probe, or made as a fusion motif or tag via a recombinant means. A preferred way to immobilize the target protein or the proteinaceous probe involves the use of the streptavidin or avidin/biotin binding pair, and any other binding moieties or agents described above.

The reaction conditions will depend on the particular interaction that is under investigation. One may vary the reaction temperature, the duration of the reaction, the buffer strength, and the target concentration or the probe concentration. For example, one may vary the concentration of the probe in order to measure its binding affinity to the target protein. To determine the thermal stability of the target-probe complex, one may vary the reaction temperature. Stability of the target-probe complex can also be determined by varying the pH, or buffer salt concentration. Where desired, the interaction can be studied under physiologically relevant temperature and buffer conditions. A physiologically relevant temperature ranges from approximately room temperature to approximately 37° C. A physiological buffer contains a physiological concentration of salt at neutral pH ranging from about 6.5 to about 7.8, and preferably from about 7.0 to about 7.5. Adjusting the reaction conditions to discern a particular interaction in vitro between a given target and a probe is within the skill of artisans in the field, and hence is not detailed herein.

The target and/or the probe are generally labeled with detectable labels so that a photon detector can detect a signal indicative of their interaction. Suitable labels encompass all of those labels disclosed in the Single-Molecule Sequencing section. Preferred labels are luminescent labels, and especially fluorescent or chromogenic labels.

In one embodiment, the target is labeled with a fluorophore whose signal is quenched upon interaction with the corresponding probe conjugated with an appropriate quencher. A variety of suitable fluorophore-quencher pairs is disclosed in the section above and hence is not detailed herein. A variation of this embodiment is to label the target and the probe with donor and acceptor fluorphores (or vise versa) that emit a distinguishable signal when the two molecules bind to each other. A wide range of applicable donor and acceptor fluorophores is also described above. Those of skill in the art will appreciate the wide diversity of detectable labels and the combinations thereof to generate a distinguishable signal that is indicative of a specific interaction between biological molecules and/or chemical compounds.

The detection of the distinguishable signal indicative of a specific interaction is performed with the aid of the optical systems described herein. Any of the systems applicable for single-molecule sequencing is equally suited for detecting interactions between other biological molecules and/or chemical compounds. A preferred system allows parallel data collection using arrays having a large number of optical confinements, where simultaneous and independent target-probe interactions can take place. In one aspect, the preferred system can collect and process signals from more than $10^4$ optical confinements, more than $2 \times 10^4$ optical confinements, more than $10^5$ optical confinements, more than $2 \times 10^5$ optical confinements, preferably more than $10^6$, or preferably more than $2 \times 10^6$ optical confinements, and even more preferably more than $10^7$ or $2 \times 10^7$ optical confinements.

Of particular significance is the application of the aforementioned method in detecting the presence of a specific protein-protein interaction. Such application generally employs a proteinaceous probe and a target protein placed in an optical confinement. In one aspect of this embodiment, the specific protein-protein interaction is between a cell surface receptor and its corresponding ligand. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions. In another aspect, the specific protein-protein interaction involves a cell surface receptor and an immunoliposome or an immunotoxin. In yet another aspect, the specific protein-protein interaction may involve a cytosolic protein, a nuclear protein, a chaperon protein, or proteins anchored on other intracellular membranous structures. In yet another aspect, the specific protein-protein interaction is between a target protein (e.g., an antigen) and an antibody specific for that antigen.

The specific interaction between an antigen and an antibody has been explored in the context of immunoassays. There exists a variety of immunoassays in the art, but none of which permits single-molecule detection. For instance, the conventional radioimmunoassay detects the interactions between a population of antigens and a population of radioactively labeled antibodies on an immunoblot. Another conventional immunoassay termed ELISA (Enzyme Llinked Immunoradiometric Assay) utilizes an antigen-specific antibody and an enzyme-lined generic antibody that binds to the specific antibody. The specific interaction between the antigen and the antibody is visualized upon addition of the substrate to the linked enzyme. Such assay again is performed on an immunoblot providing an ensemble measurement of all interactions detected.

The subject optical confinement provides an effective tool for conducting a single-molecule immunoassay. Unlike the conventional immunoassays, the specific interaction between the antigen and the antibody can be resolved at the single-molecule level. While all of the optical confinements embodied in the present invention are applicable for conducting single-molecule immunoassays, a particularly desirable system comprises an array of optical confinements with a relatively high fill fraction ratio. For example, a preferred system comprises an array of waveguides having a fill fraction greater than 0.0001, more preferably greater than about 0.001, more preferably greater than about 0.01, and even more preferably greater than 0.1.

In practicing the subject immunoassays, the antibodies an be labeled with a suitable label selected from radioactive labels, fluorescent labels, chemiluminescent labels, enzyme tags, such as digoxigenin, β-galactosidase, urease, alkaline phosphatase or peroxidase, avidin/biotin complex, and any of the detectable labels disclosed herein.

The subject immunoassays can be performed to characterize biological entities, screen for antibody therapeutics, and determine the structural conformations of a target antigen. For instance, immuoassays involving antibodies that are specific for the biological entity or specific for a by-product produced by the biological entity have been routinely used to identify the entity by forming an antibody-entity complex. Immunoassays are also employed to screen for antibodies capable of activating or down-regulating the biological activity of a target antigen of therapeutic potential. Immunoassays are also useful for determining structural conformations by using anti-idotypic antibodies capable of differentiating target proteins folded in different conformations.

Another important application of the aforementioned single-molecule analysis is to study enzyme kinetics, which may include determining the enzymatic turnover cycle, the dynamic behavior, folding and unfolding intermediates, and binding affinities. The enzymes under investigation may be immobilized within the optical confinements or present in solutions confined within the subject optical confinements.

All of the optical confinements embodied by the present invention can be employed to study enzyme kinetics. The choice of a specific optical confinement will depend on the specific characteristic that is under investigation. For instance, an optical confinement comprising a non-cylindrical core having an opening on the upper surface that is narrower than that of the base of the optical confinement is preferable for measuring the association rate constant (on-rate) of an enzymatic reaction. This configuration significantly restricts the diffusion of reactants or substrates, and hence increases the average residence time in the observation volume. On the other hand, an optical confinement comprising a core with an opening that is wider in lateral dimension than the base imposes impose a stearic or entropic hinderence to entering the structure, hence is useful for measuring the accessibility for large enzymes or enzymatic complexes.

Uses of the Subject Optical Confinements in Ensemble Measurements:

While the optical confinements of the present invention are particularly useful in conducting single-molecule analyses, the subject confinements are also suited for high throughput performance of ensemble bulk measurements. Accordingly, the present invention provides a method of detecting interactions among a plurality of molecules, comprising: placing said plurality of molecules in close proximity to an array of zero-mode waveguides, wherein individual waveguides in said array are separated by a distance sufficient to yield a detectable intensity of diffractive scattering at multiple diffracted orders upon illuminating said array with an incident wavelength of light beam; illuminating said array of zero-mode waveguides with said incident wavelength; and detecting a change in said intensity of diffractive scattering of said incident wavelength at said multiple diffracted orders, thereby detecting said interactions among said plurality of molecules.

Arrays employed for this method typically comprises optical confinements spaced far apart relative to the incident wavelength. Such spacing of the individual optical confinements far apart relative to the illuminating radiation (e.g., half of the wavelength of the illuminating radiation) creates a larger effect on the diffractive scattering of incident light at a given angle away from the angle of specula reflection. In one aspect of this embodiment, the arrays contain individual confinements separated by more than one wavelength of the incident radiation, usually more than 1.5 times the incident wavelength, but usually does not exceed 150 times the incident wavelength.

Arrays having the optical confinements spaced far apart relative to the incident wavelength also have desirable properties. While the angle-dependent scattering may raise the background signal that could be disadvantageous for certain applications, it provides a means particularly suited for characterizing the size and shape of the optical confinements. It also readily permits ensemble bulk measurements of molecule interactions, involving especially unlabelled molecules. Arrays suited for such applications generally contain individual confinements separated by more than one wavelength of the incident radiation, usually more than 1.5 times the incident wavelength, but usually not exceeding 150 times the incident wavelength.

The ensemble bulk measurement is typically performed with the aid of the optical systems described herein. Any of the setup applicable for single-molecule sequencing is equally suited for this analysis.

Further illustrations of the fabrication of the optical confinements of the present invention and then uses in sequencing are provided in the Example section below. The examples are provided as a guide to a practitioner of ordinary skill in the art, and are not meant to be limiting in any way.

EXAMPLES

Example 1

The following provides an illustrative process of fabricating zero-mode waveguide. The parameters described herein are meant to be illustrative and not intended to be limiting in any manner.

1. Substrates: Substrates are double polished, 60/40 scratch/dig surface quality, Fused Silica wafers, cut to 100 millimeters(+/−0.2 mm) diameter, and 175 micrometer(+/−25 micrometers) thick and a total thickness variation of less than 25 micrometers.

2. Clean: A mix of 5 parts deionized water, 1 part of (30% v/v Hydrogen Peroxide in water), 1 part of (30% v/v Ammonium Hydroxide in water) is heated to 75 degree Celsius on a hotplate. The wafers are immersed in the mix using a Teflon holder or other chemically resistant holder for a duration of 15 minutes.

3. Rinsing: The holder containing the wafers is removed from the RCA clean bath and immersed in a bath of deionized water. The wafers are left in this second bath for a 2 minutes period. The holder still containing the wafers is removed from the bath, and sprayed with deionized water to thoroughly finish the rinsing process.
4. Drying: Within a minute of the final rinsing step, the wafers are dried, while still in the holder, using a dry clean nitrogen flow.
5. Oxygen Plasma: The wafers are then placed in a Glenn 1000 p plasma Asher, used in plasma etch mode (wafers on a powered shelf, and under another powered shelf), with 140 mTorr pressure and 400 Watts of forward power at 40 kHz frequency. The plasma is maintained for 10 minutes. A flow of 18 sccm of molecular oxygen is used.
6. Vapor Priming: The wafers are loaded within 3 minutes after the Oxygen plasma in a Yield Engineering Systems vapor priming oven where they are coated with a layer of HexaMethylDiSilazane (HMDS) adhesion promoter.
7. Electron beam resist coating: The wafers are coated within 15 minutes after the Vapor Priming in a manual spinner unit using NEB-31 electron beam resist (Sumitomo Chemical America). About 3 ml are dispensed on the wafer, which is then spun at 4500 rpm for 60 seconds. Initial acceleration and deceleration are set to 3 seconds
8. Resist Bake: The wafers are baked on a CEE hotplate at a temperature of 115 degree Celsius for 2 minutes. The plate is equipped with a vacuum mechanism that allows good thermal contact between the wafers and the hotplate surface.
9. Gold Evaporation: a layer of 10 nm of gold is then thermally evaporated on the Wafers, on the side coated with the resist. A pressure of less than 2 10 e-06 Torr must be reached before the evaporation. The evaporation is performed at a rate of approximately 2.5 Angstrom per second and monitored using an Inficon controller.
10. Electron beam exposure: a pattern consisting of Zero Mode Waveguides is exposed on the wafers, using a high resolution electron beam lithography tool such as a Leica VB6-HR system. Zero mode waveguides are patterned as single exel features. At a current of nominally 1 nanoAmpere, and a Variable Resolution Unit of 1, and for an exel setting of 5 nanometers, doses can range from 10000 microCoulombs per square centimeters to 300000 microCoulombs per square centimeters.
11. Post Exposure Bake: The wafers are then submitted to a 2 minute post exposure bake on a hotplate at 95 degree Celsius, equally equipped with a vacuum mechanism.
12. Gold Etch: After removal from the electron beam system, the 10 nanometer gold layer is removed using gold etchant TFA at room temperature (GE 8148, Transene Corporation), for 10 seconds. Wafers are held in a Teflon holder similar to the one used in step 2.
13. Rinsing: The holder containing the wafers is removed from the gold etchant bath and immerse in a bath of deionized water. The wafers are left in this second bath for a 2 minutes period or shorter with gentle manual agitation. The holder still containing the wafers is removed from the bath, and sprayed with deionized water to thoroughly finish the rinsing process. Alternatively, the holder still containing the wafer is then placed into a new container containing fresh deionized water.
14. Drying: Within a minute of the final rinsing step, the wafers are dried, while still in the holder, using dry clean nitrogen flow.
15. Post Exposure Bake: The wafers are then submitted to a 2 minute post exposure bake on a hotplate at 95 degree Celsius, equally equipped with a vacuum mechanism.
16. Developing: The wafers still in the chemically resistant holder are immersed in developer MF-321 (Shipley Chemicals, Rohm-Haas) at room temperature for duration of 30 seconds.
17. Rinsing: The holder containing the wafers is removed from the developer etchant bath and immerse in a bath of deionized water. The wafers are left in this second bath for a 2 minutes period with gentle manual agitation. The holder still containing the wafers is removed from the bath, and sprayed with deionized water to thoroughly finish the rinsing process.
18. Drying: Within a minute of the final rinsing step, the wafers are dried, while still in the holder, using dry clean nitrogen flow.
19. Surface Descum: The wafers are loaded in a Glenn 1000 p plasma asher run in ashing mode (Wafers on a grounded plate below a powered plate), and submitted to a 30 seconds surface descuming oxygen plasma at a pressure of 140 mTorr and a power of 100 Watts forward power at 40 kHz. A flow of 18 sccm of molecular oxygen is used.
20. Aluminium Evaporation: The wafers are loading in a metal evaporator within 5 minutes of the surface descum process. A layer of 100 nm of thermally evaporated Aluminium is now deposited on the wafers. Evaporation is made at a pressure of no less than $2 \cdot 10^{-6}$ Torr at a rate of 25 Angstrom per seconds and monitored using an Inficon controller.
21. Aluminium Thickness measurement: The thickness of the aluminium is measured using a P-10 Profilometer (Tencor).
22. Zero Mode Waveguide Decasting: The Zero Mode Waveguide are decasted from the enclosing Aluminium film by immersing them, in a Teflon holder or other chemically resistant holder, in a bath of 1165 Stripper (Shipley Chemicals, Rohm-Haas), or in a bath of AZ-300T Stripper (Shipley Chemicals, Rohm-Haas). The bath is submitted to sonication by immersing the Container holding both the Stripper and the wafer holder in a sonicator. The wafers are left in the decasting bath for 30 minutes or longer for about 45 minutes, and are provided with additional gentle agitation.
23. Rinsing: The stripping bath is removed from the sonicator. The wafers are removed from the stripper bath and immerse in a bath of deionized water. The wafers are left in this second bath for a 2 minutes period with gentle manual agitation. The wafers are removed from the bath, and sprayed with deionized water to thoroughly finish the rinsing process.
24. Drying: Within a minute of the final rinsing step, the wafers are dried, while still in the holder, using dry clean nitrogen flow
25. Photoresist coating: The wafers are coated with Shipley 1827 photoresist spun at a speed of 1500 rpm. About 5 ml of resist is dispensed. Acceleration and deceleration is set to 5 seconds.

26. Resist Bake: The wafers are baked on a CEE hotplate at a temperature of 115 degree Celsius for 15 minutes. The plate is equipped with a vacuum mechanism that allows good thermal contact between the wafers and the hotplate surface.
27. Dicing: The wafer are diced using a K&S-7100 dicing saw (Kulicke & Soffa) using a resin/diamond blade (ADT 00777-1030-010-QIP 600). The wafers are mounted on a low-tack adhesive tape prior to dicing.
28. Die Removal: The dies are removed from the adhesive tape manually and stored.
29. Resist removal: The layer of 1827 photoresist is removed by immersing the dies first in an acetone bath for 1 minute, then in a 2-propanol bath for 2 minute with gentle manual agitation.
30. Die Drying: The die is dried after being removed from the 2-propanol bath using dry clean air.
31. Plasma Clean: The wafers are loaded in a Drytek 100 plasma etcher, and submitted to a 1 minute oxygen plasma at a pressure of 140 mTorr, a molecular oxygen flow of 85 sccm oxygen and an RF power of 500 Watts forward power at 13 Mhz. Alternatively, Harrick Plasma Cleaner PDC-32G are submitted to a 5 minute dry clean air plasma at a pressure of 2 Torr and 10.5 Watts of power.

Example 2

Monitoring Enzymatic Synthesis of a DNA Strand by a Single DNA Polymerase Molecule in Real Time This experiment can be performed using the optical system and reaction mixtures detailed below. However, the reference to any particular optical system and parameter, buffer, reagent, concentration, pH, temperature, or the like, is not intended to be limiting. They are included to provide as one illustrative example of carrying out the methods of the present invention.

Figure 9:
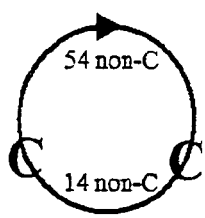
FIG. 9 depicts a single-molecule DNA sequence pattern recognition in ZMWs using artificial pre-formed replication forks.
Figure 9:
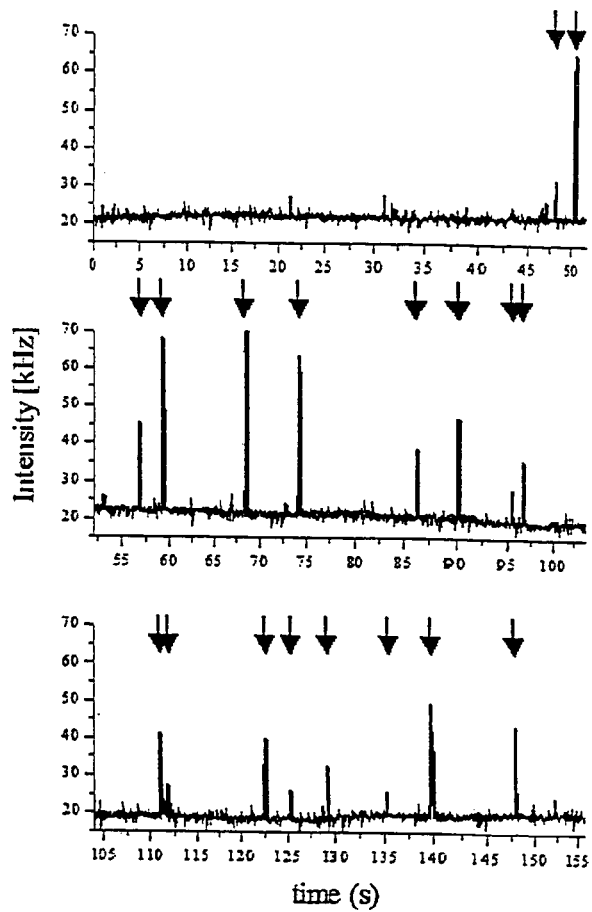
Figure 9:
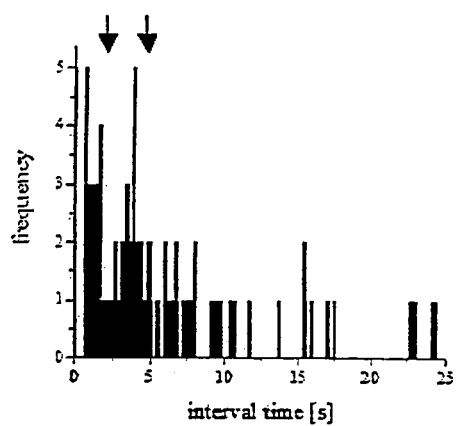

Enzymatic synthesis of a DNA strand by a single DNA polymerase molecule was tracked in real time using a fluorescently labeled nucleotides. Individual Phi29$^{N62D}$ DNA polymerase enzymes (Amersham Biosciences, Piscataway, N.J.) were immobilized in zero-mode waveguides (ZMWs) by non-specific binding using a dilute enzyme solution. After immobilization, the ZMW structures were washed to remove unbound enzyme, and then exposed to a solution containing the reaction reagents. As of the DNA template, a 70-bp pre-primed circular DNA sequence was used that contained two guanine bases in characteristic, asymmetric spacing (FIG. 9A). Strand-displacement polymerizing enzymes such as Phi29 DNA polymerase will continuously loop around the circular template and thus generate a long and highly repetitive complementary DNA strand.

An R110-dCTP (Amersham Biosciences, Piscataway, N.J.) was used as the fluorescently-tagged nucleotide analog in which the fluorophore is attached to the nucleotide via a linker to the gamma-phosphate. In contrast to the more commonly used base-labeled nucleotide analogs, gamma-phosphate-linked analogs are cleaved through the enzymatic activity of DNA polymerase as the attached nucleotide is incorporated into the growing DNA strand and the label is then free to diffuse out of the effective observation volume surrounding the DNA polymerase. The efficient removal of the fluorophore ensures continuously low background levels and prevents significant interference with DNA polymerase activity. These features of the gamma-phosphate-linked fluorophore are preferable for this application because they will enable replacement of all four bases with fluorophore-tagged analogs. Binding of a nucleotide and its subsequent incorporation into nucleic acid from a mismatch event is distinguished because the rate constants of these two processes are significantly different, and because nucleotide incorporation involves several successive steps that prevent zero delay time events.

All other nucleotides were supplied without labels. We have established a very effective way of removing any remaining trace amount of native dNTP in a nucleotide analog preparation to ensure that errors are not introduced due to the incorporation of unlabeled dNTPs by an enzymatic purification using an alkaline phosphatase prior to the polymerization assay.

To investigate the speed and processivity of the Phi29$^{N62D}$ DNA polymerase under these conditions, the incorporation characteristics were measured using R110-dCTP completely replacing dCTP in the reaction mixture, both in solution and with enzyme immobilized on a glass surface. It was found that the enzyme efficiently utilized this analog, synthesizing complementary DNA of many thousands of base pairs in length without interruption in a rolling circle synthesis protocol, using both small preformed replication forks (FIG. 9A) as well as larger circular DNA such as M13 DNA. Only two, asymmetrically spaced R110-dCTPs were to be incorporated into this template. Similar experiments demonstrated that DNA polymerase can be immobilized to the bottom of ZMWs without losing this catalytic activity.

The incorporation of the fluorescently labeled dCTP nucleotide was tracked during rolling-circle DNA synthesis by recording the fluorescent light bursts emitted in an individual ZMW. DNA polymerase activity was observed in many waveguides as distinct bursts of fluorescence, which lasted several minutes. The fluorescence time trace showed a characteristic double burst pattern (FIG. 9B), each burst corresponding to an incorporation event of a R110-dCTP analog into the DNA strand and subsequent cleavage of the fluorophore. In histograms of burst intervals derived from the full time trace, two peaks corresponding to DNA synthesis along the short (14 bases, approximately one second) and long (54 bases, approximately four seconds) DNA template segments are visible, consistent with an overall average speed measured in bulk solution under these conditions of approximately ten base pairs per second.

It is noteworthy that this single-molecule activity at a fluorophore concentration of 10 μM was readily observable. In conventionally created excitation volumes, the number of fluorophores would be far too high to permit the observation of individual enzymatic turnovers of DNA polymerase. These experiments thus confirmed the validity of the ZMW-based single-molecule DNA sequencing approach by verifying that (a) immobilization of DNA polymerase in ZMWs does not affect its enzymatic activity; (b) fluorescent gamma-phosphate-linked nucleotide analogs do not inhibit the activity of DNA polymerase; and (c) ZMWs provide an adequate degree of confinement to detect single-molecule DNA polymerase activity at physiological concentrations of reagents. More generally, these results prove that ZMWs allow single-molecule analysis of enzyme kinetics, especially involving any enzyme that can be attached to the surface and for which substrates can be fluorescently labeled.

Example 3

Real Sequencing Using Multiple Different Labeled Nucleotides

An experiment similar to that described in Example 2, above, was performed using two different labeled nucleotide analogs. The experiment can be performed using the optical setup or system and reaction mixtures detailed as follows. However, the reference to any particular optical setup and parameter, buffer, reagent, concentration, pH, temperature, or the like, is not intended to be limiting. They are included to provide as one illustrative example of carrying out the methods of the present invention.

Preparing reaction samples: Approximately 10 μl of reaction mixture is used in one sequencing reaction. The reaction mixture generally contains 0.5-1 mM $MnCl_2$, 0.1-1 uM DNA template, 10 μM dATP, 10 μM dGTP, 10 μM SAP-treated Alexa 488-dC4P, and 10 μM SAP-treated Alexa 568-dT4P, and DNA polymerase. The labeled dC4P and dT4P can also be substituted with labeled dA4P and dG4P.

Preparing Zero-mode waveguide: Prior to the polymerization reaction, a zero-mode waveguide is typically refreshed in a plasma cleaner. A PDMS gasket covering the ZMW is placed onto the waveguide to cover the individual optical confinements. An aliquot of the reaction mixture described above except the DNA polymerase is applied without touching the waveguide surface. The diffusion background is measured. If the background (i.e., fluorescence burst from the ZMW) low and acceptable, then DNA polymerase will be applied to ZMW and immobilized thereon. The immobilization mixture typically contains 0.5 to 1 MM $MnCl_2$, 0.1 to 1 uM template, 15 nM DNA polymerase, in a buffer of 25 mM Tris-HCL, pH 7.5 and 10 mM beta-mercaptoethanol. The polymerase is allowed to stick to the surface of ZMW after an incubation of about 15 minutes at about 0° C. The immobilization reaction mixture is then removed, replaced with the reaction mixture described above.

A microscope system equipped with an appropriate laser, e.g., Ar/Kr laser, is used that includes an optical setup for simultaneous collection and detection of signals from multiple different waveguides, and for the resolution of each of the A488 and 568 fluorophores present. The system includes an objective lens and a series of dichroics/notch-off filters for separating emitted fluorescence from reflected excitation light. The emitted signals are passed through a wedge filter to spatially separate the signal component of each fluorophore, and each signal is imaged onto an EMCCD camera.

Polymerase Activity Measurement: The ZMW is placed under the microscope. Polymerization reaction is then monitored using a camera for a desired period of time, e.g., two minutes or longer, after the transillumination light is applied. The data is automatically transmitted to a computer that stores and trace the fluorescence burst of each reaction in the ZMW.

Figure 16:
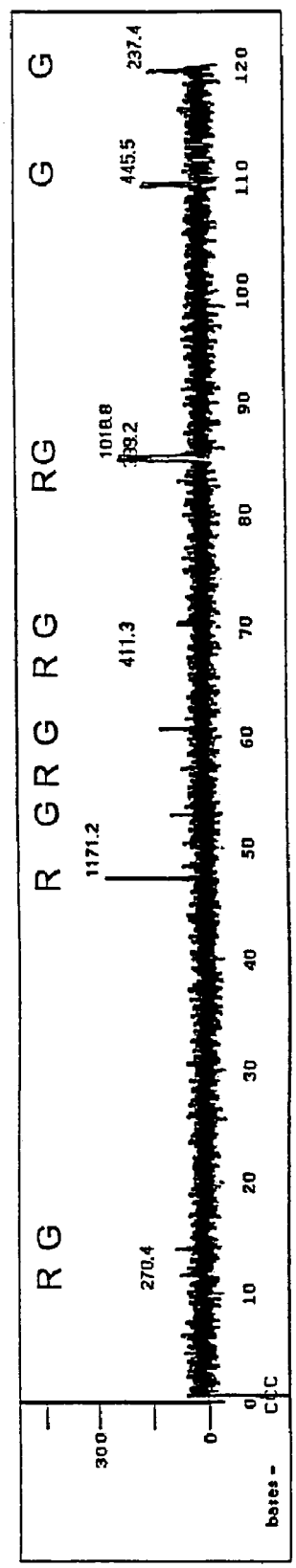
FIG. 16 depicts an exemplary profile of fluorescent bursts corresponding to the time sequence of incorporation of two types of labeled nucleotides or nucleotide analogs in single-molecule sequencing reaction using the subject optical confinement.

A circular DNA having either a block of repeating A bases followed by a block of G bases, or a series of repeating A-G bases was sequenced according to the aforementioned procedures. A representative profile of the fluorescence bursts corresponding to each incorporation event of the labeled nucleotides is depicted in FIG. 16, which indicates that real-time and single-molecule sequencing has been achieved with more than one type of labeled nucleotides. Statistical analysis of pulse data from multiple separate repeats and multiple different waveguides establishes the sequence dependant detection of incorporation of labeled bases in real time.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

The invention claimed is:

1. An apparatus comprising:
    an array of waveguides on a solid support, said array having a fill fraction greater than about 0.0001, wherein said waveguides are suitable for holding a biological reagent, and wherein said waveguides provide an effective observation volume that permits observation of individual molecules present in said biological reagent; and
    an optical system operatively coupled to the waveguides that detects signals from the effective observation volume of said waveguides.

2. The apparatus of claim 1, wherein said array has a fill fraction greater than about 0.001.

3. The apparatus of claim 1, wherein said array has a fill fraction greater than about 0.01.

4. The apparatus of claim 1, wherein said array has a fill fraction greater than about 0.1.

5. The apparatus of claim 1, wherein said array has a fill fraction ranging from about 0.001 to about 0.1.

6. The apparatus of claim 1, wherein said biological reagent comprises an enzyme, and substrates of said enzyme present at a concentration of about Michaelis constant (Km) of said enzyme for said substrates.

7. The apparatus of claim 6, wherein said concentration is higher than about 1 micromolar.

8. The apparatus of claim 6, wherein said concentration is higher than about 50 micromolar.

9. The apparatus of claim 6, wherein said concentration is higher than about 100 micromolar.

10. The apparatus of claim 6, wherein said substrates are labeled.

11. The apparatus of claim 6, wherein said individual molecules are products of a reaction between said enzyme and said substrates contained in said biological reagent.

12. The apparatus of claim 1, wherein said individual molecules are DNA/polymerase complexes.

13. The apparatus of claim 1, wherein said individual molecules are biomolecules selected from the group consisting of nucleic acids, polypeptides, and combinations thereof.

14. The apparatus of claim 1, wherein said individual molecules are organic or inorganic chemical compounds.

15. The apparatus of claim 1, wherein said individual molecules are labeled with a detectable label.

16. The apparatus of claim 15, wherein said detectable label is selected from the group consisting of a fluorescent label, a chemiluminescent label, and a radioactive label.

17. The apparatus of claim 1, wherein said waveguides are made of porous film.

18. The apparatus of claim 1, wherein said waveguides are operatively coupled to an optical transmission element transmitting an incident light beam.

19. The apparatus of claim 18, wherein said optical transmission element comprises an element selected from the group consisting of a microlens, a nanolens, an arrayed waveguide grating, an optical switch, an optical fiber, an optical attenuator, a polarization filter, a wave plate, and a delay line.

20. The apparatus of claim 1, wherein said optical system further comprises a photon detector.

21. The apparatus of claim 20, wherein said photon detector is selected from the group consisting of an optical reader, a high efficiency photon detection system, a photodiode, a camera, a charge coupled device, an electron-multiplying charge coupled device, and an intensified charge coupled device.

22. The apparatus of claim 1 that precludes propagation of a majority of an incident electromagnetic energy having a wavelength greater than a cutoff wavelength.

23. The apparatus of claim 22, wherein an individual waveguide of said array comprises a cladding surrounding a core, and wherein said individual waveguide precludes propagation of more than 90% of the incident electromagnetic energy having a wavelength greater than a cutoff wavelength through said core.

24. The apparatus of claim 22, wherein an individual waveguide of said array comprises a cladding surrounding a core, and wherein said individual waveguide precludes propagation of more than 99% of the incident electromagnetic energy having a wavelength greater than a cutoff wavelength through said core.

25. The apparatus of claim 23, wherein each individual waveguide of said array comprises a cladding surrounding a core, and wherein said individual waveguide precludes propagation of more than 90% of the incident electromagnetic energy having a wavelength greater than a cutoff wavelength through said core.

26. The apparatus of claim 22, wherein said cladding comprises a sheet, and one or more holes extending through said sheet where each hole constitutes a core of an individual waveguide.

27. The apparatus of claim 22, wherein an individual waveguide of said array comprises a cladding surrounding a core that is cylindrical.

28. The apparatus of claim 22, wherein an individual waveguide of said array comprises a cladding surrounding a core that is non-cylindrical.

29. The apparatus of claim 22, wherein said cladding comprises a metal alloy.

30. The apparatus of claim 1, wherein each individual waveguide provides an effective observation volume less than about 1000 zeptoliters.

31. The apparatus of claim 1, wherein each individual waveguide provides an effective observation volume less than about 80 zeptoliters.

32. The apparatus of claim 1, wherein each individual waveguide provides an effective observation volume less than about 10 zeptoliters.

33. A kit comprising an array of waveguides of claim 1 and an instruction manual for use of said array.

34. A method of performing multiple chemical reactions involving a plurality of reaction samples, comprising:
 (a) providing an array of waveguides of claim 1;
 (b) placing the plurality of reaction samples comprising labeled reactants into the waveguides in the array, wherein a separate reaction sample is placed into a different waveguide in the array;
 (c) subjecting the array to conditions suitable for formation of products of the chemical reactions; and
 (d) detecting the formation of the products with said optical system.

35. The method of claim 34, wherein the step of detecting comprises illuminating the different waveguides with an incident light beam and detecting an optical signal emitted from the reaction samples.

36. The method of claim 34, wherein the chemical reactions involve protein-protein interactions.

37. The method of claim 34, wherein the chemical reactions involve nucleic acid-protein interactions.

38. The method of claim 34, wherein the chemical reactions involve nucleic acid-nucleic acid interactions.

39. A method of detecting a biological analyte, comprising:
 optically capturing the analyte within an optical confinement that is created by
 (a) providing an array of waveguides having a fill fraction greater than about 0.0001; and
 (b) illuminating at least one waveguide within the array that is suspected to contain the analyte with an incident light beam thereby detecting the analyte.

40. The method of claim of claim 39, said array of waveguides having a fill fraction from about 0.001 to about 0.1.

41. The method of claim 39, wherein said fill fraction is greater than about 0.1.

42. The method of claim 39, wherein the analyte is labeled with a detectable label.

43. The method of claim 39, wherein the analyte is selected from the group consisting of nucleic acid, polypeptide, organic compound, and inorganic compound.

44. A method of sequencing a plurality of target nucleic acid molecules, comprising:
 (a) providing an array of waveguides having a fill fraction greater than about 0.0001;
 (b) mixing in the waveguides the plurality of target nucleic acid molecules, primers complementary to the target nucleic acid molecules, polymerization enzymes, and more than one type of nucleotides or nucleotide analogs to be incorporated into a plurality of nascent nucleotide strands, each strand being complementary to a respective target nucleic acid molecule;
 (c) subjecting the mixture of step (b) to a polymerization reaction under conditions suitable for formation of the nascent nucleotide strands by template-directed polymerization of the nucleotides or nucleotide analogs;
 (d) illuminating the waveguides with an incident light beam; and
 (e) identifying the nucleotides or the nucleotide analogs incorporated into the each nascent nucleotide strand.

45. The method of claim 44, wherein the step of identifying yields a time sequence of incorporation of the nucleotides provided in step (b).

46. The method of claim 44, wherein the identifying step is effected while the template-directed polymerization is taking place.

47. The method of claim 44, wherein the target nucleic acid molecules are selected from the group consisting of circular DNA molecules, linear DNA molecules, RNA molecules, and DNA/RNA hybrids.

* * * * *